(12) United States Patent
Horiba et al.

(10) Patent No.: US 10,786,217 B2
(45) Date of Patent: Sep. 29, 2020

(54) X-RAY PHASE-CONTRAST IMAGING APPARATUS

(71) Applicant: Shimadzu Corporation, Kyoto (JP)

(72) Inventors: Akira Horiba, Kyoto (JP); Taro Shirai, Kyoto (JP); Takahiro Doki, Kyoto (JP); Satoshi Sano, Kyoto (JP); Naoki Morimoto, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 90 days.

(21) Appl. No.: 16/002,517

(22) Filed: Jun. 7, 2018

(65) Prior Publication Data

US 2018/0368795 A1    Dec. 27, 2018

(30) Foreign Application Priority Data

Jun. 22, 2017  (JP) ................................. 2017-122276

(51) Int. Cl.
*A61B 6/00* (2006.01)
*G01N 23/041* (2018.01)
*G01N 23/20008* (2018.01)
*G01N 23/20* (2018.01)

(52) U.S. Cl.
CPC ............ *A61B 6/484* (2013.01); *A61B 6/4035* (2013.01); *A61B 6/4291* (2013.01); *A61B 6/54* (2013.01); *G01N 23/041* (2018.02); *G01N 23/20008* (2013.01); *G01N 23/20075* (2013.01)

(58) Field of Classification Search
CPC .................................................. A61B 6/4035
See application file for complete search history.

(56) References Cited

U.S. PATENT DOCUMENTS

| 8,755,487 | B2* | 6/2014 | Kaneko | ................. A61B 6/06 |
|  |  |  |  | 378/36 |
| 2012/0153181 | A1* | 6/2012 | Iwakiri | ............... A61B 6/4291 |
|  |  |  |  | 250/394 |
| 2013/0142308 | A1* | 6/2013 | Ishii | ..................... G01N 23/04 |
|  |  |  |  | 378/62 |
| 2016/0349197 | A1* | 12/2016 | Kitamura | ........ G01N 23/20008 |

FOREIGN PATENT DOCUMENTS

| JP | 2012-110606 A | 6/2012 |
| JP | 2016-050891 | 4/2016 |
| WO | 2014/030115 A1 | 2/2014 |
| WO | WO 2017/094294 | 8/2017 |

OTHER PUBLICATIONS

Extended European Search Report dated Nov. 26, 2018 in the corresponding European patent application No. 18177512.3.
Notice of Reasons for Refusal dated Jun. 2, 2020 for corresponding Japanese application No. 2017-122276, submitted with a machine translation.

* cited by examiner

*Primary Examiner* — Yara B Green
(74) *Attorney, Agent, or Firm* — Muir Patent Law, PLLC

(57) ABSTRACT

This X-ray phase-contrast imaging apparatus is equipped with a plurality of gratings and grating holders for holding the plurality of gratings. The plurality of gratings is arranged such that the extending direction of grating components of the plurality of gratings is oriented in a direction in which the positional displacement due to the grating holder becomes maximum in a plane orthogonal to an optical axis of the X-ray.

9 Claims, 17 Drawing Sheets

First Embodiment

First Embodiment

First Embodiment

First Embodiment

First Embodiment

First Embodiment

First Embodiment

Positional relation when self-image position is relatively displaced in the vertical (Y-axis) direction Since the positional displacement occurs in the scanning direction, the shape of the step curve is changed, which affects image

First Embodiment

Positional relation when self-image position is relatively displaced in the vertical (Y-axis) direction Since no positional displacement occurs in the scanning direction, the shape of the step curve is not changed

Second Embodiment

First Modification of First Embodiment

Second Modification of First Embodiment

X-RAY PHASE-CONTRAST IMAGING APPARATUS

CROSS-REFERENCE TO RELATED APPLICATIONS

The priority application number JP2017-122276, entitled "X-RAY PHASE-CONTRAST IMAGING APPARATUS", filed on Jun. 22, 2017, invented by Akira Horiba, Taro Shirai, Takahiro Doki, Satoshi Sano, Naoki Morimoto, upon which this patent application is based is hereby incorporated by reference.

BACKGROUND OF THE INVENTION

Field of the Invention

The present invention relates to an X-ray phase-contrast imaging apparatus, and more particularly to an X-ray phase-contrast imaging apparatus for generating an absorption image, a phase differential image, and a dark field image by a Talbot interferometer.

Background Technique

Conventionally, an X-ray phase-contrast imaging apparatus for generating an absorption image, a phase differential image, and a dark field image by a Talbot interferometer is known. Such an X-ray phase-contrast imaging apparatus is disclosed in, for example, International Publication No. WO No. 2014-030115.

The X-ray phase-contrast imaging apparatus disclosed in International Publication No. WO 2014/030115 is equipped with an X-ray source, a multi-slit, a phase grating, an absorption grating, a detector, and a stepping arrangement for moving the phase grating stepwise. The X-ray phase-contrast imaging apparatus disclosed in International Publication No. WO 2014/030115 can generate a phase differential image and a dark field image in addition to the absorption image by capturing an image by moving the phase grating stepwise.

Note that the "phase differential image" is an image imaged based on a phase shift of an X-ray occurred when the X-ray passes through an object. The "dark field image" denotes a visibility image obtained by a visibility change based on small-angle scattering of an object. Further, the dark field image is also called a small-angle scattering image. The "visibility" denotes sharpness.

Here, in a Talbot interferometer, it is designed such that the period of the absorption grating becomes the same as the period of the self-image of the phase grating formed at a position away from the phase grating by a given distance (Talbot distance). In a Talbot interferometer, each grating is held by a grating holder including a moving mechanism for adjusting the initial position of the grating or translating the grating at the time of imaging. In a Talbot interferometer, a phase differential image and a dark field image can be generated by capturing images while translating the absorption grating in a direction orthogonal to the extending direction of the grating component by a specified distance.

Note that the "grating component" denotes an X-ray transmission portion and an X-ray shielding portion (X-ray phase change portion) of the grating.

In a Talbot interferometer, imaging is performed while moving the phase grating or the absorption grating stepwise to thereby acquire a detection signal curve (hereinafter referred to as "step curve") of the X-ray to be detected in each pixel of the detector. Then, in a Talbot interferometer, the phase differential image and the dark field image can be generated based on the step curve obtained by imaging with no object arranged and the step curve obtained by imaging with an object arranged.

However, in the X-ray phase-contrast imaging apparatus disclosed in International Publication No. WO 2014/030115, when each grating causes a positional displacement in a plane orthogonal to the optical axis direction of the X-ray due to the grating holder for holding the grating during imaging, displacement occurs in the relative position between the self-image of the phase grating and the absorption grating. When a positional displacement in a direction orthogonal to the extending direction of the grating component of the grating occurs in the relative position between the self-image of the phase grating and the absorption grating, the shape of the step curve to be obtained changes, which causes a problem that the image quality of the phase differential image and the dark field image to be generated deteriorates.

The present invention has been made to solve the aforementioned problems, and an object of the present invention is to provide an X-ray phase-contrast imaging apparatus capable of suppressing deterioration of image quality of an image to be acquired even in cases where a grating causes a positional displacement due to a grating holder in a plane orthogonal to an optical axis direction of an X-ray.

SUMMARY OF THE INVENTION

In order to attain the aforementioned object, an X-ray phase-contrast imaging apparatus according to an aspect of the present invention includes an X-ray source; a detector configured to detect an X-ray irradiated from the X-ray source; a plurality of gratings arranged between the X-ray source and the detector; a control unit configured to generate an image based a detection signal of the X-ray that has passed through the plurality of gratings and detected by the detector; and grating holders each configured to hold each of the plurality of gratings, wherein the plurality of gratings is arranged such that an extending direction of grating components of the plurality of gratings is oriented in a direction in which a positional displacement due to the grating holder becomes maximum in a plane orthogonal to an optical axis of the X-ray.

Here, in a Talbot interferometer, when a grating causes a positional displacement due to a grating holder, the self-image of the grating also causes a positional displacement. When a positional displacement due to the grating holder occurs in a direction orthogonal to the extending direction of the grating component of the grating, a positional displacement of the self-image of the grating occurs with respect to the scanning direction of the grating. Therefore, when the positional displacement of the grating occurs during the acquisition of the step curve, the shape of the step curve changes. On the other hand, when a positional displacement due to the grating holder occurs in the extending direction of the grating component of the grating, the positional displacement does not affect in a direction orthogonal to the extending direction of the grating component of the grating. Therefore, the shape of the step curve to be obtained does not change.

Therefore, according to the present invention, as described above, the grating is arranged so that the extending direction of the grating component of the grating is oriented in the direction of the positional displacement due to the grating holder. With this, even if a positional displacement due to the grating holder occurs in a plane orthogonal to the optical axis direction of the X-ray, it becomes possible to suppress the change of the positional relationship between the self-image of the phase grating and the absorption grating in a direction orthogonal to the extending direction of the grating component of the absorption grating. As a result, it is possible to suppress the change of the shape of the step curve to be obtained. Thus, the image quality of the image to be acquired can be suppressed from being deteriorated even when the grating causes a positional displacement due to the grating holder in a plane orthogonal to the optical axis direction of the X-ray.

In the X-ray phase-contrast imaging apparatus according to the aforementioned one aspect of the present invention, it is preferably configured such that the grating holder is further equipped with a grating position adjustment mechanism for adjusting a relative position of the plurality of gratings, the control unit is configured to adjust the relative position of the plurality of gratings by the grating position adjustment mechanism, and the grating position adjustment mechanism is configured to relatively move the plurality of gratings along a direction orthogonal to a direction in which a positional displacement of the grating holder becomes maximum at the time of imaging.

With this configuration, the direction in which a plurality of gratings is relatively moved and the direction of the positional displacement due to the grating holder can be made orthogonal. Therefore, even when a positional displacement occurs due to the grating holder, the positional displacement in the direction in which a plurality of gratings is moved relatively can be suppressed. As a result, it is possible to suppress the change of the shape of the step curve to be obtained, which can suppress deterioration of the image quality of the image to be generated.

In this case, it is preferable that the grating position adjustment mechanism is configured by stacking a plurality of positioning mechanisms for moving the plurality of gratings in different directions, and the plurality of gratings are arranged such that the extending direction of the grating components of the plurality of gratings is oriented in a direction in which a total thickness of the grating position adjustment mechanisms becomes maximum.

Here, in cases where the grating position adjustment mechanism is composed of the same members, for example, the positional displacement of the grating when the grating causes a positional displacement due to the thermal deformation of the grating position adjustment mechanism is considered to depend on the thickness of the grating position adjustment mechanism. Therefore, when it is configured to arrange such that the extending direction of the grating components of the plurality of gratings is oriented in the direction in which the thickness of the grating position adjustment mechanism becomes maximum, it is possible to analytically determine the direction of the positional displacement without measuring the positional displacement due to the grating position adjustment mechanism.

In the configuration in which imaging is performed while relatively moving a plurality of gratings along a direction orthogonal to a direction in which the positional displacement of the grating holder becomes maximum, it is preferable that the plurality of gratings includes a first grating for generating a Talbot interference by changing a phase of the X-ray irradiated from the X-ray source and a second grating for shielding a part of the X-ray forming an image generated by the Talbot interference by the first grating, and the first grating and the second grating are arranged such that the extending direction of both grating components of the first grating and the second grating is oriented in a direction in which the positional displacement due to the grating holder becomes maximum in the plane orthogonal to the optical axis of the X-ray.

With this configuration, in a Talbot interferometer requiring strict setting of the positional relationship between the first grating and the second grating, it is possible to suppress deterioration of the image quality of the image due to the positional displacement of the first grating and/or the second grating due to the grating holder. Therefore, in a Talbot interferometer, it is preferable to use the present invention to suppress the deterioration of the image quality of the image due to the positional displacement of the first grating and/or the second grating due to the grating holder.

In the configuration in which imaging is performed while relatively moving a plurality of gratings along a direction orthogonal to a direction in which the positional displacement of the grating holder becomes maximum, it is preferable that the plurality of gratings includes a third grating for shielding a part of the X-ray irradiated from the X-ray source and a fourth grating for shielding a part of the X-ray forming an image generated by shielding a part of the X-ray by the third grating, and the third grating and the fourth grating are arranged such that the extending direction of both grating components of the third grating and the fourth grating is oriented in a direction in which the positional displacement due to the grating holder becomes maximum in the plane orthogonal to an optical axis of the X-ray.

With such a configuration, in a non-interferometer, deterioration of the image quality of the image due to the positional displacement of the grating holder can be suppressed. Therefore, in a non-interferometer, the deterioration of the image quality due to the positional displacement of the third grating and/or the fourth grating due to the grating holder can be suppressed. Therefore, in a non-interferometer, it is preferable to use the present invention to suppress the deterioration of the image quality of the image due to the positional displacement of the third grating and/or the fourth grating due to the grating holder.

In the X-ray phase-contrast imaging apparatus according to the aforementioned one aspect of the present invention, it is preferably configured such that the positional displacement due to the grating holder includes a positional displacement due to at least thermal deformation of the grating holder.

With this configuration, even in cases where the grating holder is thermally deformed due to thermal fluctuations occurred around the grating holder during imaging of the X-ray phase-contrast imaging image, it is possible to suppress the deterioration of the image quality of the image to be acquired by the positional displacement of the grating due to the grating holder.

In the X-ray phase-contrast imaging apparatus according to the aforementioned one aspect of the present invention, it is preferably configured such that the direction of the positional displacement due to the grating holder is a direction in which a positional displacement amount is larger among the positional displacement amounts obtained by decomposing the positional displacement amount of the grating holder in two different directions in a plane orthogonal to the optical axis of the X-ray irradiated from the X-ray source.

With this configuration, it becomes possible to regard one direction in which the positional displacement amount of the grating holder, which most affects the positional displacement of the grating, as a direction of the positional displacement of the grating holder. As a result, it is possible to easily determine the arrangement direction of the grating.

In this case, it is preferable that the X-ray source, the plurality of gratings, and the detector are arranged in a horizontal direction or a vertical direction, and the direction of the positional displacement due to the grating holder is a direction in which the positional displacement amount is larger among two directions including the vertical direction and the lateral direction of the detector in the plane orthogonal to the optical axis of the X-ray irradiated from the X-ray source.

With such a configuration, even in cases where the X-ray phase-contrast imaging apparatus is arranged in either the horizontal direction or the vertical direction, it is enough to move the grating to either one of the vertical direction and the lateral direction of the detector in a plane orthogonal to the optical axis of the X-ray, the movement of the grating by the grating position adjustment mechanism can be performed easily.

In the X-ray phase-contrast imaging apparatus according to the aforementioned one aspect of the present invention, it is preferable that the plurality of gratings further include a fifth grating for enhancing spatial coherence of the X-ray by shielding a part of the X-ray irradiated from the X-ray source.

With this configuration, it is possible to improve the coherence of the X-ray source by using the fifth grating. As a result, the X-ray phase-contrast image capturing can be performed using the X-ray source whose focal length is not very small, so that the freedom of selection of the X-ray source can be enhanced.

DESCRIPTION OF PREFERRED EMBODIMENTS

Hereinafter, some embodiments of the present invention will be described with reference to the drawings.

First Embodiment

With reference to FIG. 1 to FIG. 10, a configuration of an X-ray phase-contrast imaging system 100 according to a first embodiment of the present invention will be described.
(Configuration of X-Ray Phase-Contrast Imaging Apparatus)

With reference to FIG. 1 to FIG. 6, the configuration of the X-ray phase-contrast imaging apparatus 100 according to the first embodiment will be described.

Figure 1:
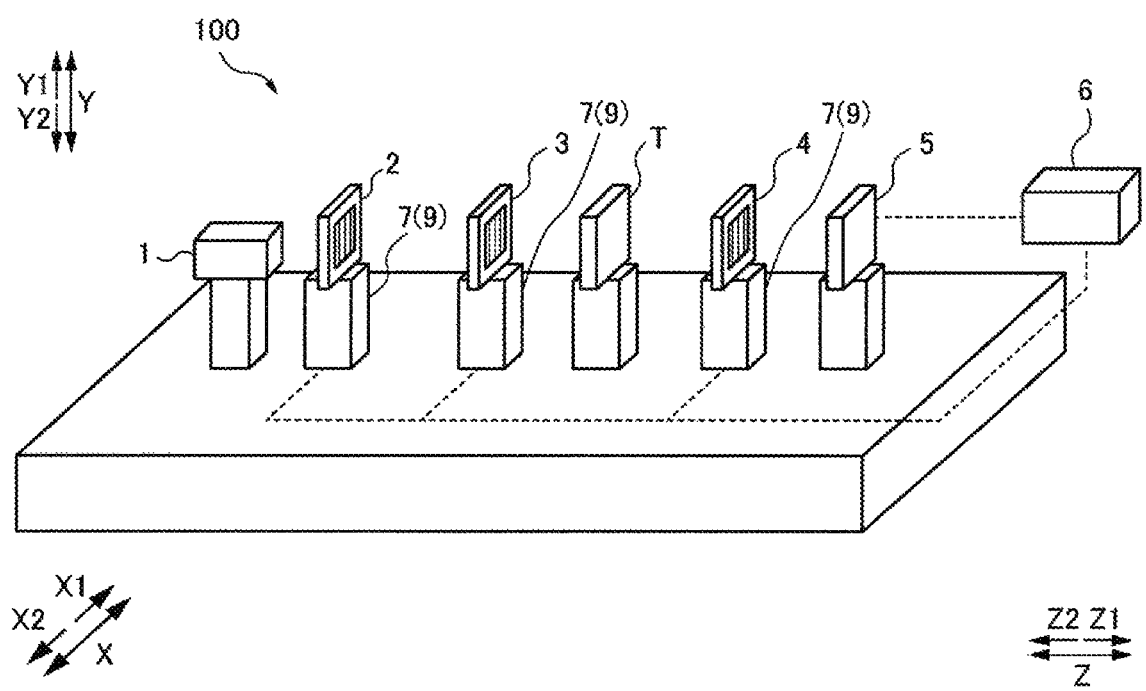
FIG. 1 is a diagram showing an overall structure of an X-ray phase-contrast imaging apparatus according to a first embodiment of the present invention.

As shown in FIG. 1, the X-ray phase-contrast imaging apparatus 100 is an apparatus for imaging an inside of an object T by utilizing the diffusion of the X-ray that has passed through the object T. Further, the X-ray phase-contrast imaging apparatus 100 is a device for imaging the inside of the object T by utilizing a Talbot effect. For example, in nondestructive inspection applications, it can be used for imaging the inside of the object T as an object. Further, for example, in medical applications, the X-ray phase-contrast imaging apparatus 100 can be used for imaging the inside of the object T as a living body.

Figure 2:
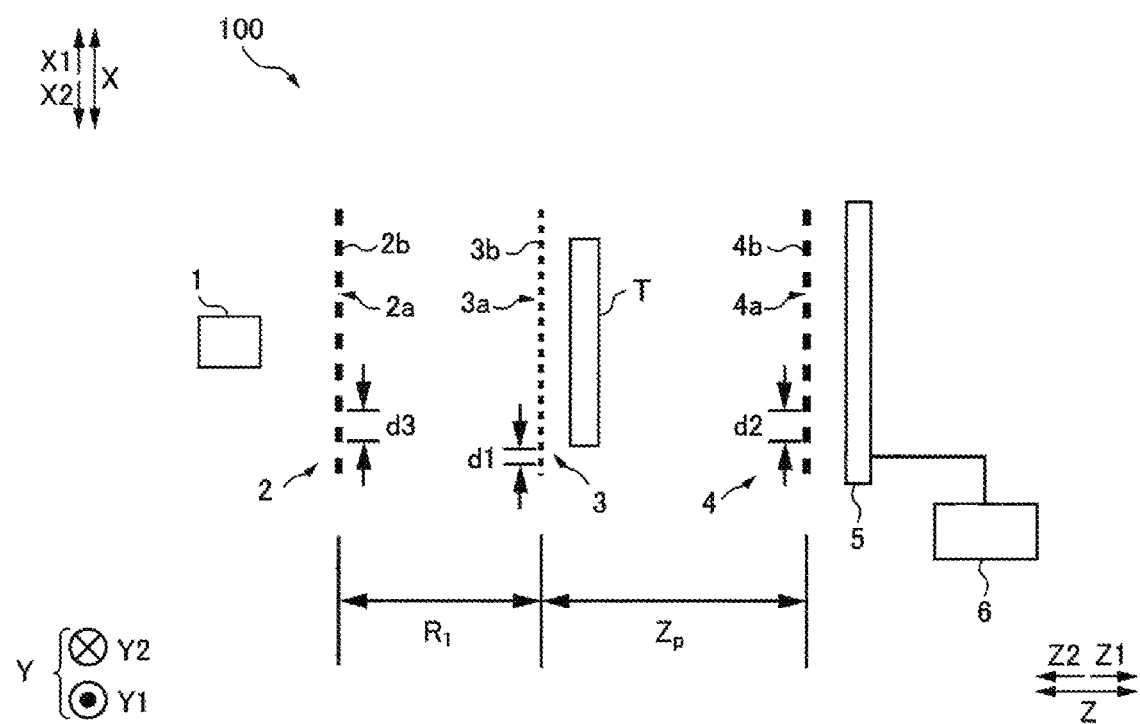
FIG. 2 is a schematic diagram for explaining an arrangement of an X-ray source, a plurality of gratings, and a detector of the X-ray phase-contrast imaging apparatus according to the first embodiment of the present invention.

FIG. 1 is a perspective view of the X-ray phase-contrast imaging apparatus 100. Further, FIG. 2 is a view of the X-ray phase-contrast imaging apparatus 100 as viewed from above (Y1-direction). As shown in FIG. 1, the X-ray phase-contrast imaging apparatus 100 is equipped with an X-ray source 1, a third grating 2, a first grating 3, a second grating 4, a detector 5, a control unit 6, and grating holders 7.

In this specification, the vertical direction is defined as a Y-direction, the vertical upward direction is defined as a Y1-direction, and the vertical downward direction is defined as a Y2-direction. Further, two orthogonal directions in a horizontal plane orthogonal to the Y-direction are defined as an X-direction and a Z-direction. Of the X-direction, one direction thereof is defined as an X1-direction and the other direction is defined as an X2-direction. Further, of the Z-direction, one direction thereof is defined as a Z1-direction and the other direction is defined as a Z2-direction. In the example shown in FIG. 1, the X-ray source 1, the plurality of gratings, and the detector 5 are arranged side by side in the Z1-direction. Note that the Z-direction is an example of the "optical axis direction of the X-ray" recited in claims.

The X-ray source 1 is configured to generate an X-ray by being applied by a high voltage and irradiate the generated X-ray in the Z1-direction.

As shown in FIG. 2, the third grating 2 has a plurality of X-ray transmission portions 2a and X-ray shielding portions 2b. The X-ray transmission portion 2a and the X-ray shielding portion 2b are each formed so as to extend linearly. Further, the X-ray transmission portion 2a and the X-ray shielding portion 2b are arranged at a predetermined period (pitch) $d_3$ in a direction orthogonal to the extending direction of the X-ray transmission portion 2a and the X-ray shielding portion 2b. Note that the X-ray transmission portion 2a and the X-ray shielding portion 2b are each an example of the "grating component" recited in claims.

The third grating 2 is arranged between the X-ray source 1 and the first grating 3 and enhances the spatial coherence of the X-ray by shielding a part of the X-ray irradiated from the X-ray source 1. The third grating 2 is a so-called multi-slit. Note that the third grating 2 is an example of the "fifth grating" recited in claims.

The first grating 3 has a plurality of slits 3a and X-ray phase change portions 3b. The slit 3a and the X-ray phase change portion 3b are each formed so as to extend linearly. Further, the slit 3a and the X-ray phase change portion 3b are arranged at a predetermined period (pitch) $d_1$ in a direction orthogonal to the extending direction of the slit 3a and the X-ray phase change portion 3b. The first grating 3 is a so-called phase grating. Note that the slit 3a and the X-ray phase change portion 3b are each an example of the "grating component" recited in claims.

The first grating 3 is arranged between the X-ray source 1 and the second grating 4. The first grating 3 causes a Talbot interference by changing the phase of the X-ray emitted from the X-ray source 1. The Talbot interference denotes that when an X-ray with coherence passes through a grating in which slits are formed, a grating image (self-image 30 (see, e.g., FIG. 7)) is formed at a position away from the grating by a predetermined distance (Talbot distance $Z_p$).

The second grating 4 has a plurality of X-ray transmission portions 4a and X-ray shielding portions 4b. The X-ray transmission portion 4a and the X-ray shielding portion 4b are each formed so as to extend linearly. Further, the X-ray transmission portion 4a and the X-ray shielding portion 4b are arranged at a predetermined period (pitch) $d_2$ in a direction orthogonal to the extending direction of the X-ray transmission portion 4a and the X-ray shielding portion 4b. The second grating 4 is a so-called absorption grating. The first grating 3, the second grating 4, and the third grating 2 are gratings having different roles, respectively, but the slit 3a, the X-ray transmission portion 4a, and the X-ray transmission portion 2a each transmit the X-ray. Further, the X-ray shielding portion 4b and the X-ray shielding portion 2b each play a role of shielding the X-ray, and the X-ray phase change portion 3b changes the phase of the X-ray by the difference of the refractive index from the slit 3a. Note that the X-ray transmission portion 4a and the X-ray shielding portion 4b are each an example of the "grating component" recited in claims.

The second grating 4 is arranged between the first grating 3 and the detector 5, and is irradiated by the X-ray that has passed through the first grating 3. Further, the second grating 4 is arranged at a position away from the first grating 3 by the Talbot distance $Z_p$. The second grating 4 interferes with the self-image 30 (see FIG. 7) of the first grating 3 to form a moire fringe (not shown) on the detection surface of the detector 5.

The Talbot distance $Z_p$ is expressed by the following equation (1):

$$Z_p = p\frac{d_1^2}{\lambda} \frac{R_1}{R_1 - p\frac{d_1^2}{\lambda}} \quad (1)$$

Here, "$d_1$" is the period of the first grating 3. Further, "$\lambda$" is the wavelength of the X-ray irradiated from the X-ray source 1. "$R_1$" is the distance from the first grating 3 to the second grating 4. "p" is an arbitrary integer.

The period $d_2$ of the second grating 4 is designed to be the same period as the self-image 30 of the first grating 3 (see FIG. 7), and is expressed by the following equation (2).

$$d_2 = \frac{R_1 + Z_p}{R_1} d_1 \quad (2)$$

The detector 5 is configured to detect the X-ray, convert the detected X-ray into an electric signal, and read the converted electric signal as an image signal. The detector 5 is, for example, an FPD (Flat Panel Detector). The detector 5 is composed of a plurality of conversion elements (not shown) and a plurality of pixel electrodes (not shown) arranged on the plurality of conversion elements. The detector 5 is arranged such that the plurality of conversion elements and pixel electrodes match in the X-direction and the Y-direction in the array direction of the pixels at a predetermined period (pixel pitch). Further, the detector 5 is configured to output the obtained image signal to the control unit 6.

The control unit 6 is configured to generate an absorption image, a phase differential image, and a dark field image based on the image signal output from the detector 5. The control unit 6 includes, for example, a CPU (Central Processing Unit) and a GPU (Graphics Processing Unit).

In the first embodiment, the X-ray phase-contrast imaging apparatus 100 is configured to capture an image of the object T by a fringe scanning method. The fringe scanning method is a method in which image capturing is performed while translating the first grating 3 or the second grating 4 at a predetermined pitch, an intensity-modulated signal is generated based on the X-ray intensity detected for each pixel, and imaging is performed based on the generated intensity modulation signal.

Next, with reference to FIGS. 3 to 5, the configuration in which the grating holder 7 of the X-ray phase-contrast imaging apparatus 100 according to the first embodiment holds the grating and the configuration in which the grating position adjustment mechanism 9 adjusts the position of the grating will be described.

Figure 3:
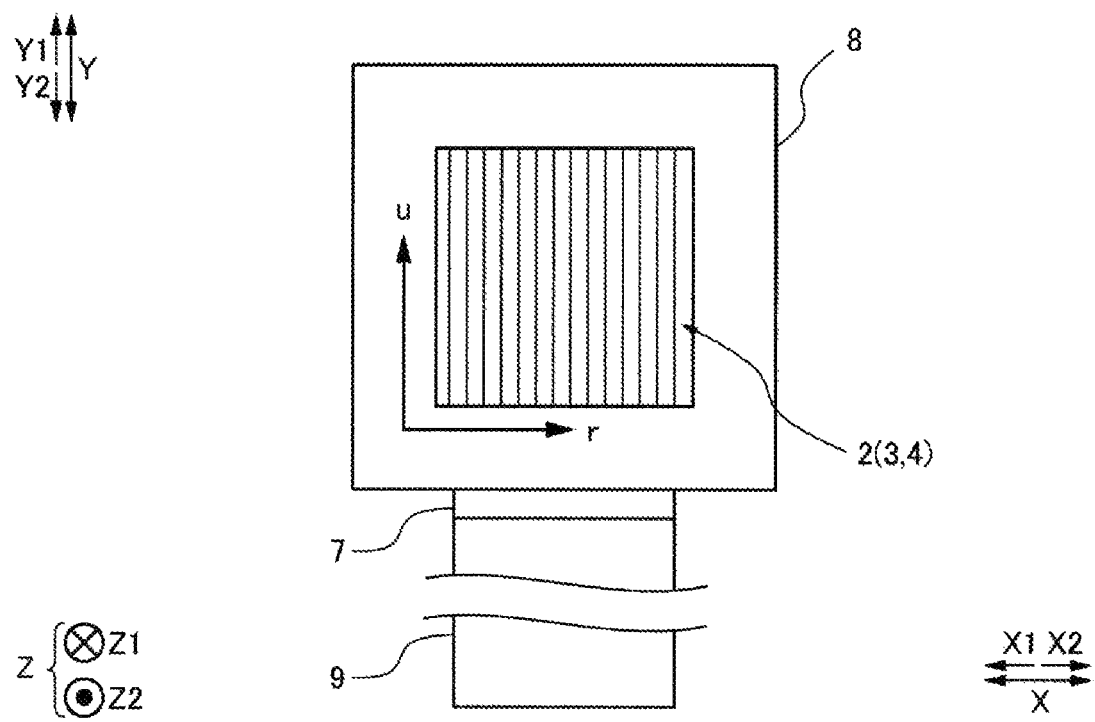
FIG. 3 is an enlarged schematic diagram of the grating and the grating holder of the X-ray phase-contrast imaging apparatus according to the first embodiment of the present invention.

FIG. 3 is an enlarged view of the grating held by the grating holder 7. As shown in FIG. 3, each grating is of a rectangular shape, and the grating component is arranged so as to extend in the u-direction. Further, the grating components of each grating are arranged in the r-direction at a predetermined period (pitch). Further, each grating is accommodated in a metal grating frame 8, and the grating holder 7 holds each grating by holding the grating frame 8. The grating frame 8 is of a rectangular frame shape, and is made of, for example, aluminum. Further, the grating holder 7 is made of a metallic member and includes a grating position adjustment mechanism 9 for adjusting the position of a plurality of gratings.

Like the grating holder 7, the grating position adjustment mechanism 9 is also composed of metal members. The grating position adjustment mechanism 9 is configured to adjust the relative position of each grating. Further, the grating position adjustment mechanism 9 is configured to scan the second grating 4 based on the signal from the control unit 6 at the time of imaging. The grating holder 7 and the grating position adjustment mechanism 9 are made of, e.g., aluminum.

In the first embodiment, the grating holder 7 (grating position adjustment mechanism 9) is provided at the arrangement location of each grating to hold each of the third grating 2, the first grating 3, and the second grating 4. In the example shown in FIG. 3, the grating holder 7 is provided on the end face of the grating position adjustment mechanism 9 in the Y1-direction, and is configured to hold the grating frame 8 from the Y1-direction.

(Configuration in which Position Adjustment Mechanism Adjusts Positional Displacement of Grating)

Next, with reference to FIG. 4 and FIG. 5, the configuration in which the grating position adjustment mechanism 9 adjusts the positional displacement of the first grating 3 and/or the second grating 4 will be described. Here, in a Talbot Lau interferometer, such as the X-ray phase-contrast imaging apparatus 100, the second grating 4 is arranged at a position away from the first grating 3 by the Talbot distance $Z_p$. Further, in cases where the relative position of the first grating 3 and the second grating 4 are displaced, an unintended moire fringe occurs, which causes problems such that the image quality of the generated image deteriorates. Therefore, in the first embodiment, the X-ray phase-contrast imaging apparatus 100 is configured to adjust the relative position of the first grating 3, the second grating 4, and the third grating 2 in advance by the grating position adjustment mechanisms 9.

Figure 4:
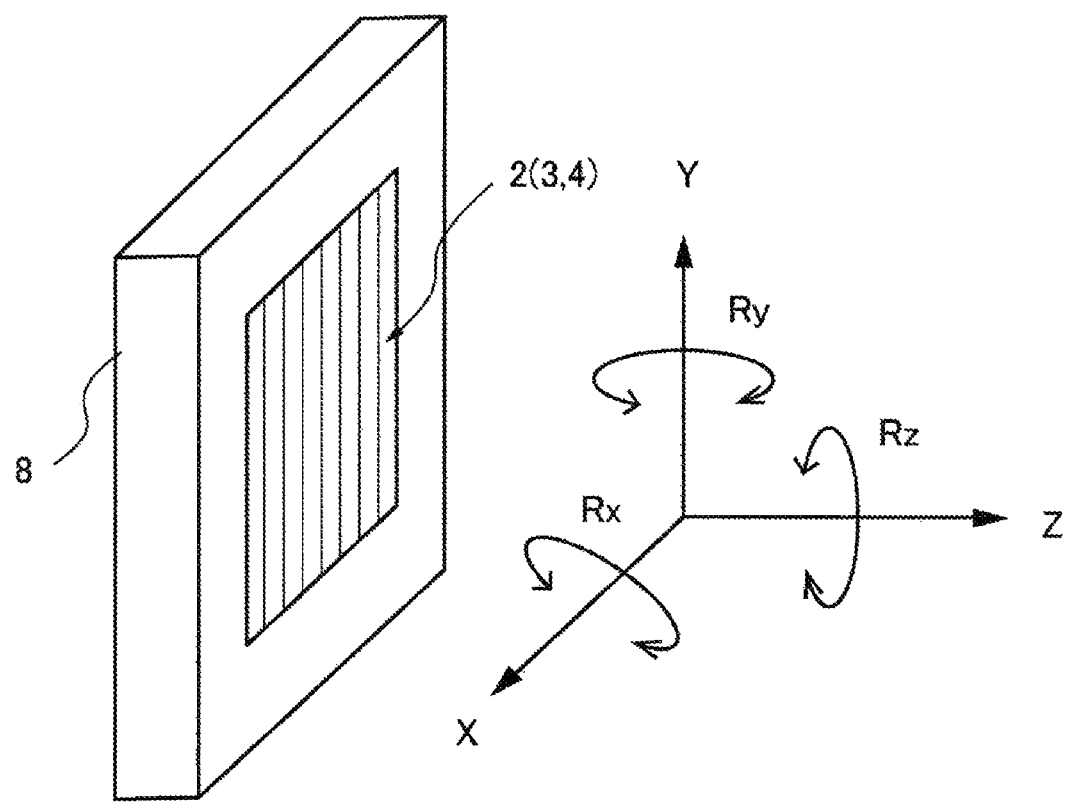
FIG. 4 is a schematic diagram for explaining the positional displacement direction of the grating to be adjusted by the grating position adjustment mechanism of the X-ray phase-contrast imaging apparatus according to the first embodiment of the present invention.

The positional displacements of the first grating 3, the second grating 4, and the third grating 2 mainly include, as shown in FIG. 4, a positional displacement in the X-direction, a positional displacement in the Y-direction, a positional displacement in the Z-direction, a positional displacement in the rotational direction Rz about the central axis in the Z-direction, a positional displacement in the rotational direction Rx about the central axis in the X-direction, and a positional displacement in the rotational direction Ry about the central axis in the Y-direction.

Figure 5:
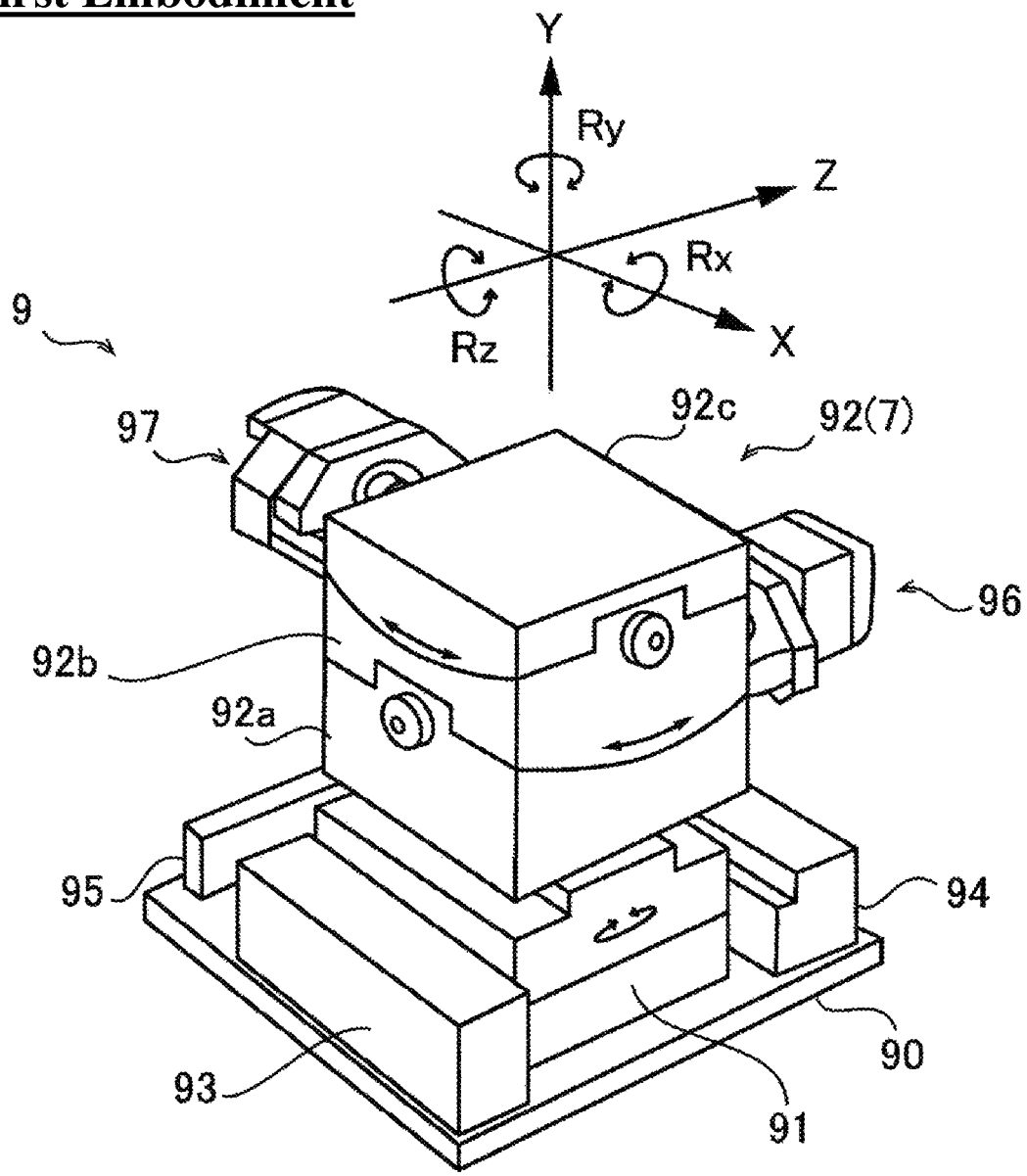
FIG. 5 is a schematic diagram for explaining a configuration of the grating position adjustment mechanism of the X-ray phase-contrast imaging apparatus according to the first embodiment of the present invention.

As shown in FIG. 5, the grating position adjustment mechanism 9 is configured by stacking a plurality of positioning mechanisms for moving the plurality of gratings in different directions. Specifically, the grating position adjustment mechanism 9 is configured so that a plurality of positioning mechanisms is stacked in the Y-direction, and is configured so that the maximum direction of the total thickness of the grating position adjustment mechanism 9 is the Y-direction. More specifically, the grating position adjustment mechanism 9 includes a base unit 90, a stage support unit 91, a stage 92 for mounting a grating, a first drive unit 93, a second drive unit 94, a third drive unit 95, a fourth drive unit 96, and a fifth drive unit 97.

The first to fifth drive units each include, for example, a motor or the like. Further, the stage 92 is composed of a connecting portion 92a, an about-Z-direction axis rotating unit 92b, and an about-X-direction axis rotating unit 92c. Further, the stage 92 is configured as a grating holder 7 for holding each grating.

The first drive unit 93, the second drive unit 94, and the third drive unit 95 are each provided on the upper surface of the base unit 90. The first drive unit 93 is configured to reciprocate the stage support unit 91 in the Z-direction. Further, the second drive unit 94 is configured to rotate the stage support unit 91 about the Y-axis direction. Further, the third drive unit 95 is configured to reciprocate the stage support unit 91 in the X-direction. The stage support unit 91 is connected to the connecting portion 92a of the stage 92. As the stage support unit 91 moves, the stage 92 also moves.

Further, the fourth drive unit 96 is configured to reciprocate the about-Z-direction axis rotating unit 92b in the X-direction. The about-Z-direction axis rotating unit 92b is formed so that the bottom surface thereof is formed into a convex curved surface toward the connecting portion 92a, and is configured to rotate the stage 92 about the central axis in the Z-direction by being reciprocated in the X-direction.

Further, the fifth drive unit 97 is configured to reciprocate the about-X-direction axis rotating unit 92c in the Z-direction. The about-X-direction axis rotating unit 92c is formed so that the bottom surface thereof is formed into a convex curved surface toward the Z-direction axis rotating unit 92b, and is configured to rotate the stage 92 about the central axis in the X-direction by being reciprocated in the Z-direction.

Therefore, the grating position adjustment mechanism 9 is configured so that the grating can be adjusted in the Z-direction by the first drive unit 93. Further, the grating position adjustment mechanism 9 is configured so that the grating can be adjusted in the rotation direction (Ry-direction) about the Y-axis direction by the second drive unit 94. Further, the grating position adjustment mechanism 9 is configured so that the grating can be adjusted in the X-direction by the third drive unit 95. Further, the grating position adjustment mechanism 9 is configured so that the grating can be adjusted in the rotation direction (Rz-direction) about the Z-direction axis by the fourth drive unit 96. Further, the grating position adjustment mechanism 9 is configured so that the grating can be adjusted in the rotation direction (Rx-direction) about the X-axis direction by the fifth drive unit 97. The movable range in each axis direction is, e.g., several mm (millimeters). Further, the rotatable angles in the rotational direction Rx about the X-direction axis, the rotational direction Ry about the Y-direction axis, and the rotational direction Rz about the Z-direction axis are each, e.g., several degrees.

Figure 6A:
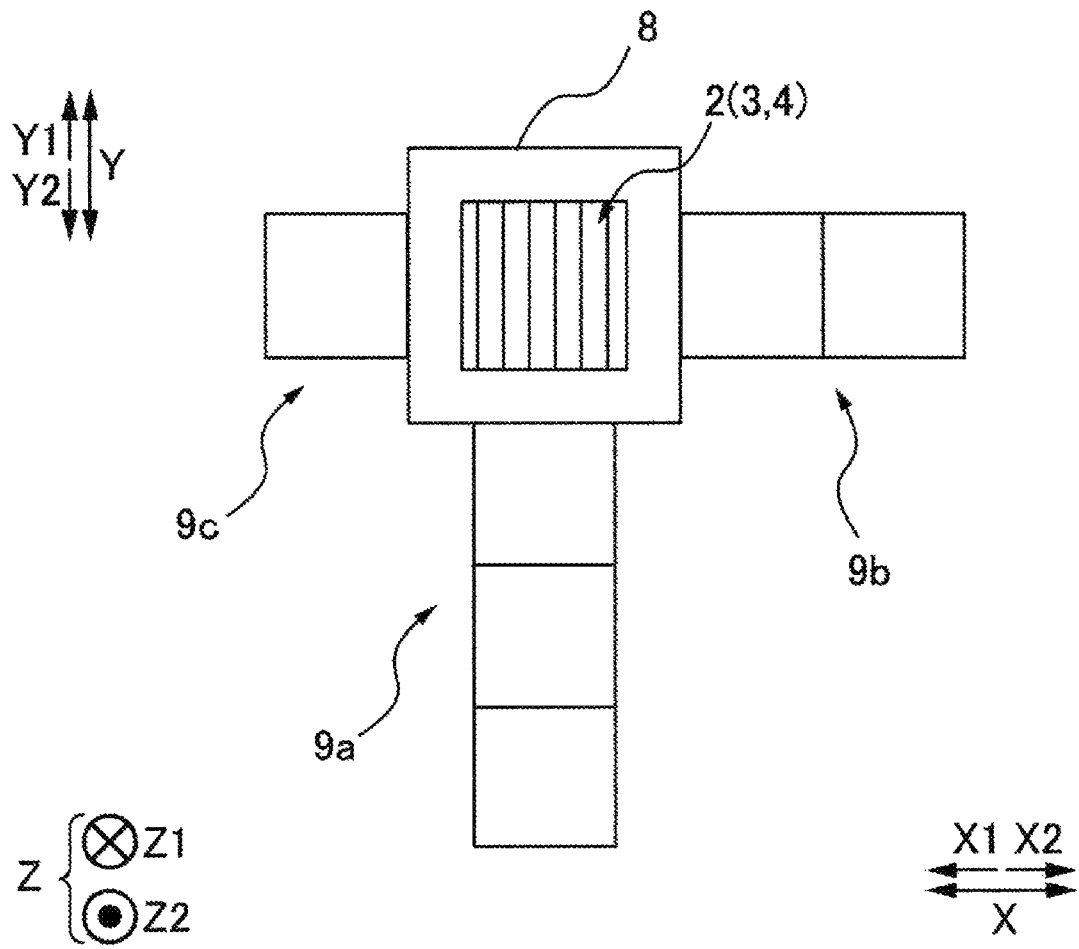
FIG. 6A is a schematic diagram for explaining a first example in which the grating holding mechanism of the X-ray phase-contrast imaging apparatus according to the first embodiment of the present invention holds the grating.
Figure 6B:
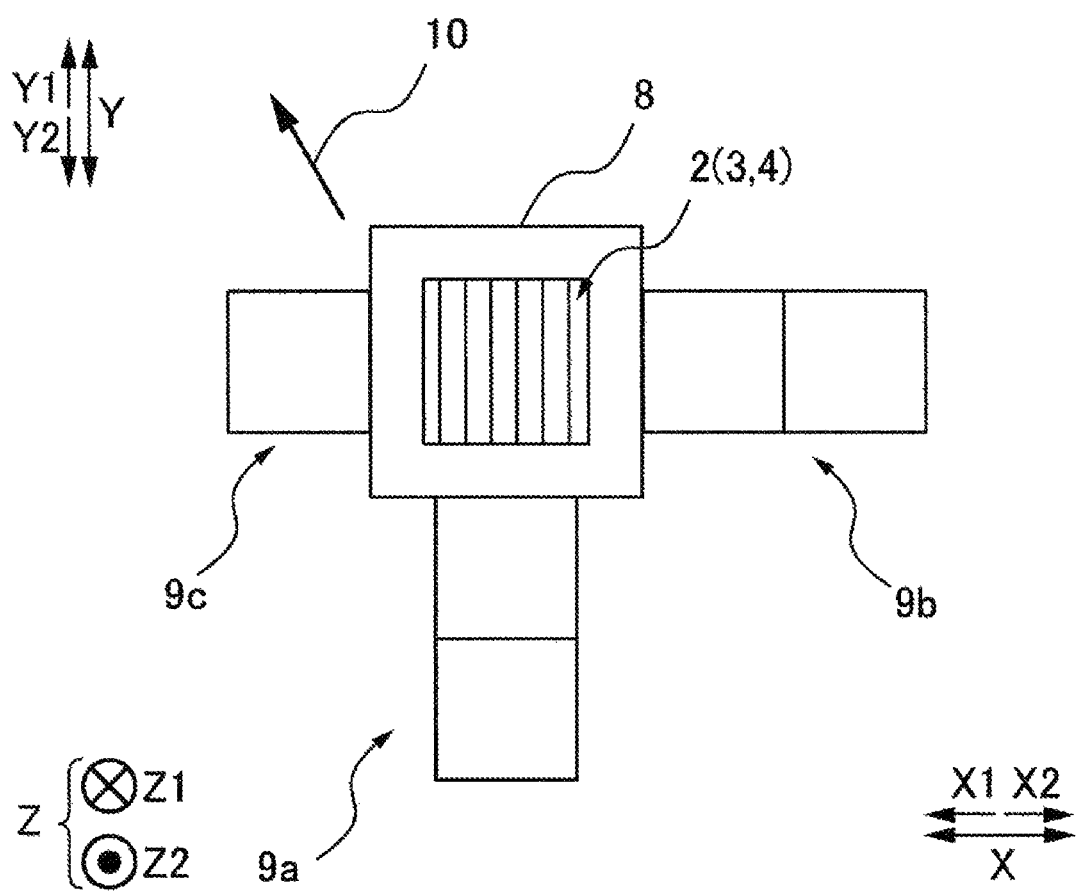
FIG. 6B is a schematic diagram for explaining a second example in which the grating holding mechanism of the X-ray phase-contrast imaging apparatus according to the first embodiment of the present invention holds the grating.

In the first embodiment, as shown in FIG. 5, the grating position adjustment mechanism 9 is configured to perform the position adjustment of the grating in the six axis directions by placing the grating on the stage 92. However, it may be configured in any way as long as the position adjustment of the grating can be performed. For example, as shown in FIG. 6A and FIG. 6B, it may be configured to hold the grating from three directions. In the example shown in FIG.

6A, the grating position adjustment mechanism 9 includes a first adjustment mechanism 9a, a second adjustment mechanism 9b, and a third adjustment mechanism 9c.

FIGS. 6A and 6B show the positioning mechanism constituting the first to third adjustment mechanisms in a rectangular shape for the sake of convenience, and the respective positioning mechanisms are shown as having the same thickness.

The first adjustment mechanism 9a is a structure in which three positioning mechanisms are stacked in the Y-direction, and is configured to adjust the position of the grating in the X-direction, Y-direction, and Z-direction. Further, the second adjustment mechanism 9b has a structure in which two positioning mechanisms are stacked in the X-direction, and is configured to adjust the position of the grating in the Rx-direction and Ry-direction. Further, the third adjustment mechanism 9c is configured to hold the grating from the X-direction by one positioning mechanism, and is configured to adjust the position of the grating in the Rz-direction. In the first embodiment, as shown in FIG. 6B, it may be configured such that the first adjustment mechanism 9a and the second adjustment mechanism 9b have the same total thickness.

(Generation of Absorption Image, Phase Differential Image, and Dark Field Image)

Next, with reference to FIG. 7 and FIG. 8, the configuration in which the control unit 6 generates an absorption image, a phase differential image, and a dark field image will be described.

Figure 7:
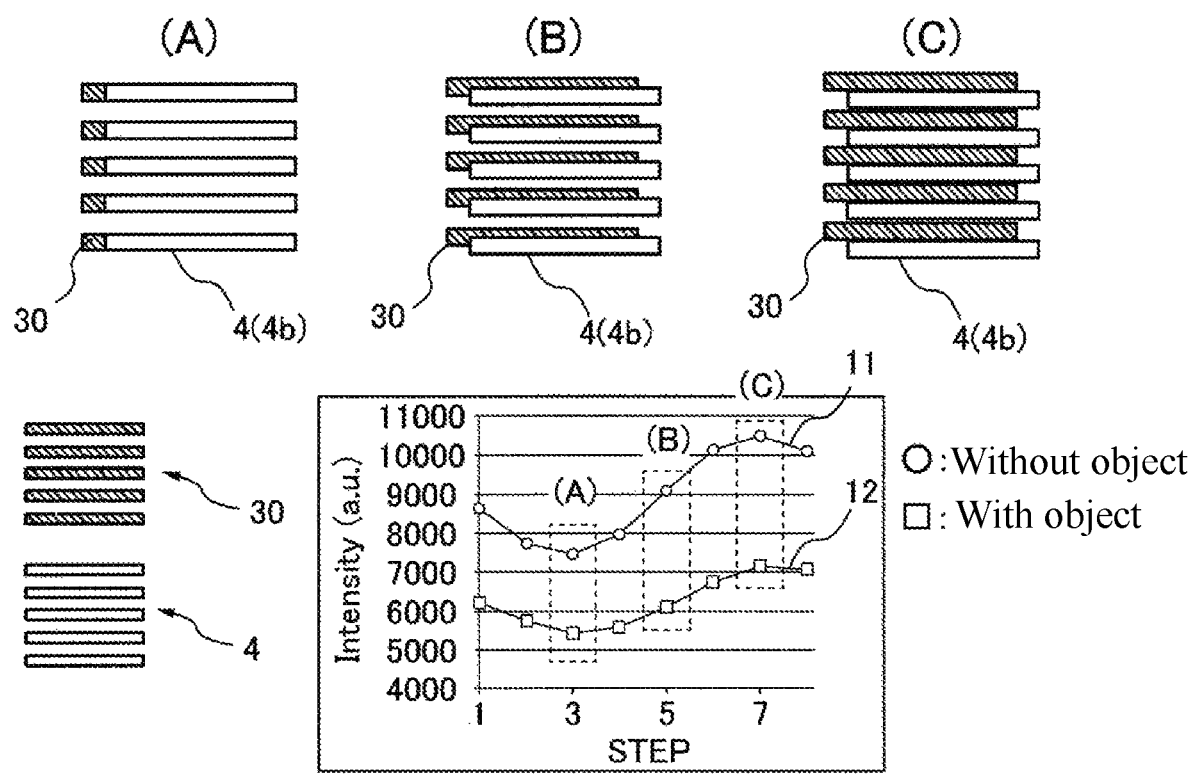
FIG. 7 is a schematic diagram for explaining a method of generating an absorption image, a phase differential image, and a dark field image in a Talbot interferometer.

FIG. 7 is a diagram showing an example of acquiring a step curve by translating the second grating 4 in a direction orthogonal to the grating component with respect to the self-image 30 of the first grating 3. In the state of (A) of FIG. 7, since the self-image 30 of the first grating 3 and the X-ray shielding portion 4b of the second grating 4 are overlapped, the intensity of the X-ray to be detected by the detector 5 becomes small. However, when it becomes the state of (B) of FIG. 7 by scanning the first grating 3, since the area where the self-image 30 of the first grating 3 overlaps the X-ray transmission portion 4a of the second grating 4 increases, the intensity of the X-ray to be detected by the detector 5 increases. When the first grating 3 is scanned until it becomes the state of (C) of FIG. 7, since the self-image 30 of the first grating 3 overlaps the X-ray transmission portion 4a of the second grating 4, the intensity of the X-ray to be detected by the detector 5 becomes maximum. In this manner, a step curve is acquired for each pixel of the detector 5.

Note that FIG. 7 shows an example of the step curve 11 obtained without arranging an object T and an example of the step curve 12 obtained by arranging an object T.

Next, with reference to FIG. 8, a configuration for generating an absorption image, a phase differential image, and a dark field image using the acquired step curve will be described.

Figure 8:
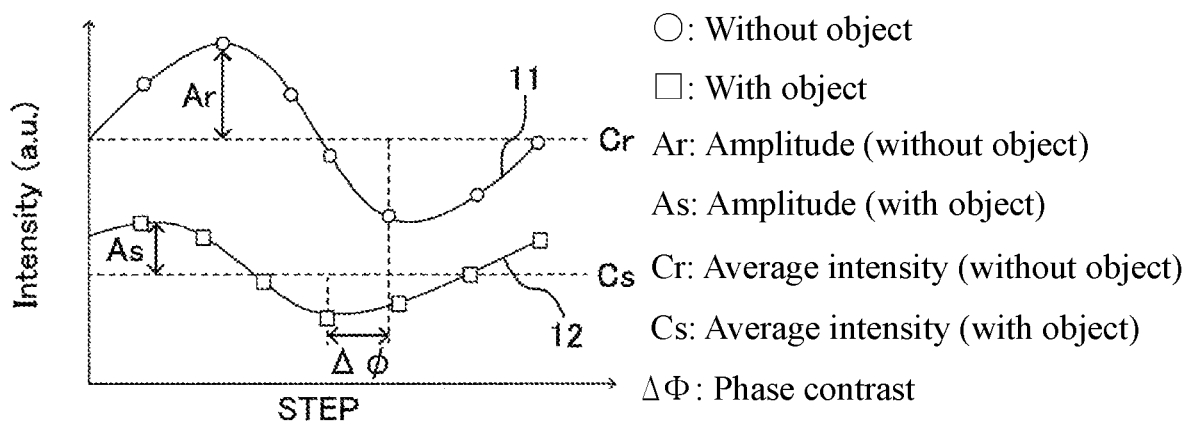
FIG. 8 is a schematic diagram for explaining a method of obtaining a step curve in a Talbot interferometer.

As shown in FIG. 8, the absorption image can be generated by the ratio of the average intensity Cs of the X-ray at the time of acquiring the image by arranging the object T and the average intensity Cr of the X-ray at the time of acquiring the image without arranging the object T. The phase differential image can be obtained by multiplying the number obtained by a predetermined calculation by the phase-contrast $\Delta\varphi$ between the step curve 11 obtained by imaging without arranging the object T and the step curve 12 obtained by imaging in a state in which the object T is arranged. Further, the dark field image can be generated by the ratio of the visibility (Vr) at the time of acquiring the image without arranging the object T and the visibility (Vs) at the time of acquiring the image with the object T arranged. Vr can be obtained from the ratio of the amplitude Ar and the average intensity Cr of the step curve 11. Further, Vs can be obtained from the ratio of the amplitude As and the average intensity Cs of the step curve 12.

(Positional Displacement of Grating)

Here, in a fringe scanning method, a step curve indicating the intensity change of the X-ray of each pixel is acquired by imaging while scanning the grating, and an image is generated based on the acquired step curve. Therefore, when the first grating 3 and/or the second grating 4 cause a positional displacement due to the grating holder 7 during the acquiring of the step curve, the relative position between the self-image 30 of the first grating and the second grating 4 changes. Therefore, there is a possibility that the intensity of the X-ray detected by the detector 5 changes. When the intensity of the detected X-ray changes, the shape of the step curve to be acquired changes, which causes a problem such that the image quality of the image to be generated deteriorates.

Therefore, with reference to FIGS. 9A, 9B, 10A and 10B, an example in which changing of the intensity of the X-ray to be detected by the relationship between the direction of the positional displacement of the grating and the scanning direction of the grating affects the step curve and an example in which the changing does not affect the step curve will be described. In the first embodiment, the positional displacement of the grating denotes a positional displacement of the grating occurred in a plane orthogonal to the optical axis of the X-ray (in the X-Y plane).

Figure 9A:
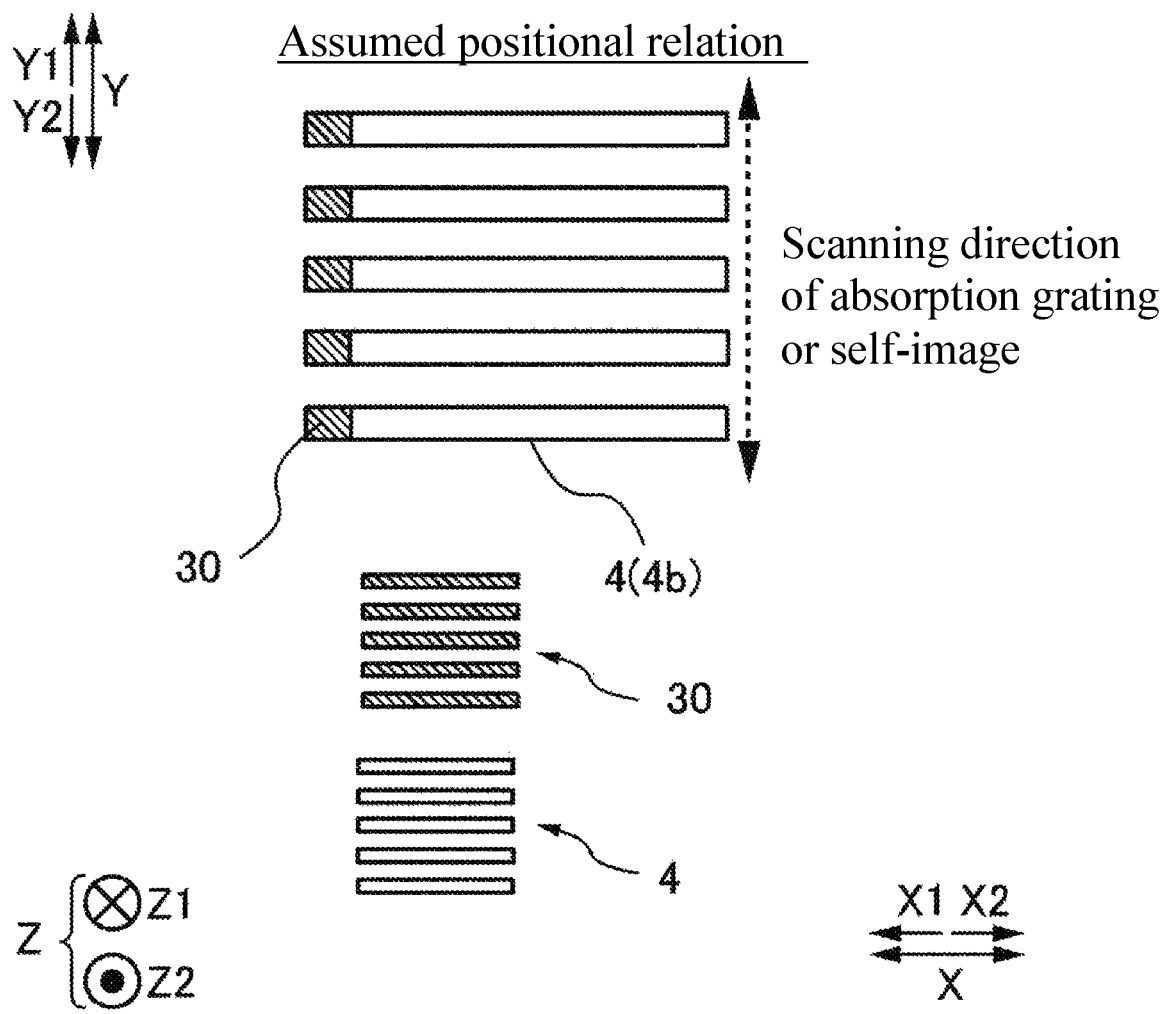
FIG. 9A is a schematic diagram for explaining assumed positions of the self-image of the first grating and the second grating when the grating components of the first grating and the second grating are arranged so as to extend in the X-direction.
Figure 9B:
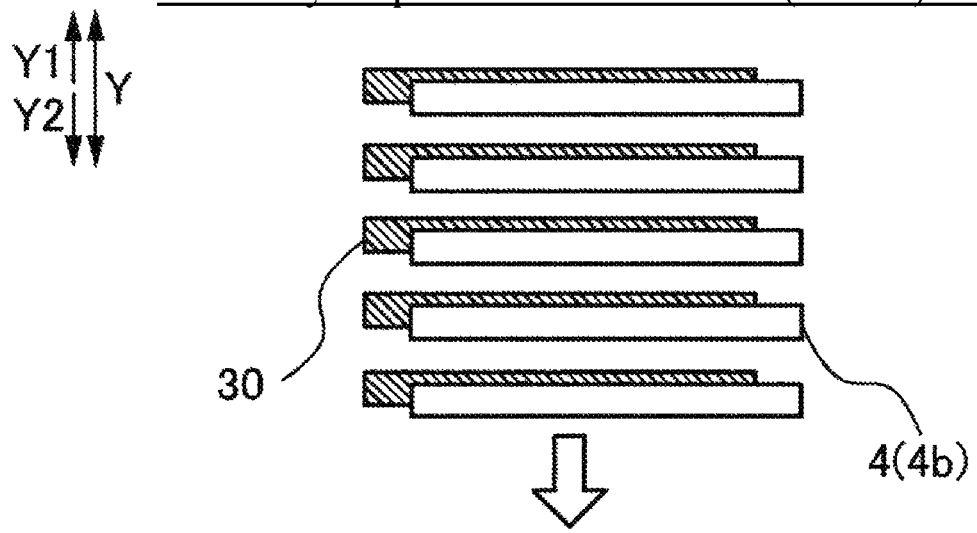
FIG. 9B is a schematic diagram for explaining the positional relationship when the position of the self-image of the first grating is displaced in the Y-direction when the grating components of the first grating and the second grating are arranged so as to extend in the X-direction.
Figure 9B:

FIG. 9 is a diagram FIGS. 9A and 9B are diagrams showing an example when the positional displacement of the grating occurred in a direction along the scanning direction of the grating. In the example shown in FIGS. 9A and 9B, the first grating 3 and the second grating 4 are arranged with the grating components of the first grating 3 and the second grating 4 oriented in the X-direction. In the fringe scanning method, the scanning direction of the grating is a direction orthogonal to the grating component, so the scanning direction of the grating is the Y-direction.

FIG. 9A is a diagram showing the positional relationship between the self-image 30 of the first grating 3 and the second grating 4 when the first grating 3 and the second grating 4 are in an assumed appropriate positional relationship. As shown in FIG. 9A, when no positioning displacement of the grating has occurred, the position in the scanning direction (Y-direction) of the grating of the self-image 30 of the first grating 3 and the X-ray shielding portion 4b of the second grating 4 coincides. Therefore, the step curve obtained by imaging while scanning the first grating 3 in the Y-direction from this state has a shape reflecting the shape of the object T.

FIG. 9B is a diagram showing the positional relationship between the self-image 30 of the first grating 3 and the second grating 4 when the first grating 3 caused the positional displacement in the Y1-direction. As shown in FIG. 9B, when a positional displacement occurred in the scanning direction of the grating, the position of the self-image 30 of the first grating 3 and the position of the X-ray shielding portion 4b of the second grating 4 in the Y-direction are displaced. Therefore, compared with the case in which the grating is arranged in an appropriate positional relationship, the intensity of the X-ray detected by the detector 5 changes. Therefore, during the acquisition of the step curve, when the first grating 3 caused a positional displacement as shown in FIG. 9B, the intensity of the X-ray to be detected by the detector 5 changes, which changes the shape of the step curve. That is, it becomes a step curve including the X-ray intensity changes other than the X-ray intensity change due to the shape of the object T.

Figure 10A:
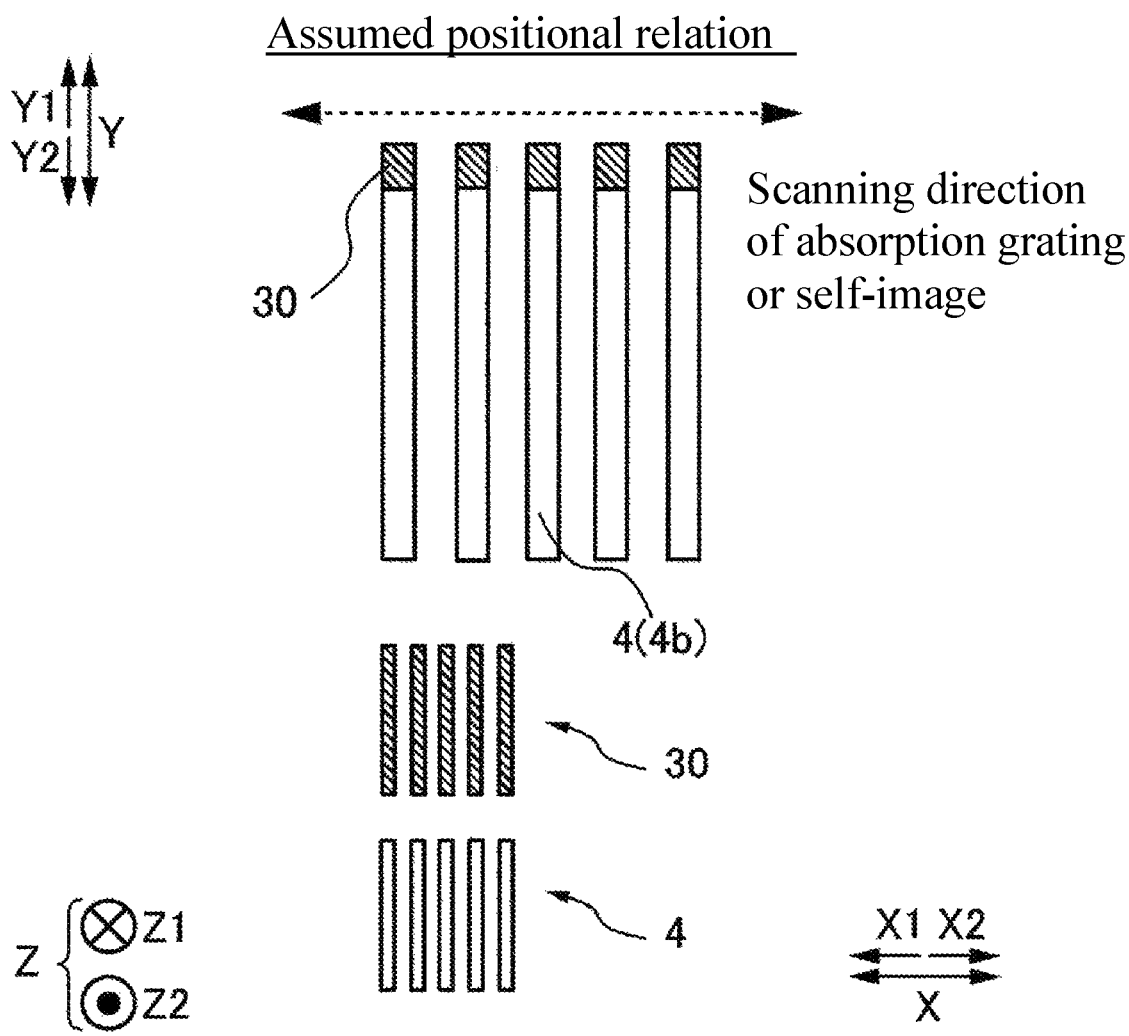
FIG. 10A is a schematic diagram for explaining assumed positions of the self-image of the first grating and the second grating when the grating components of the first grating and the second grating are arranged so as to extend in the Y-direction.
Figure 10B:
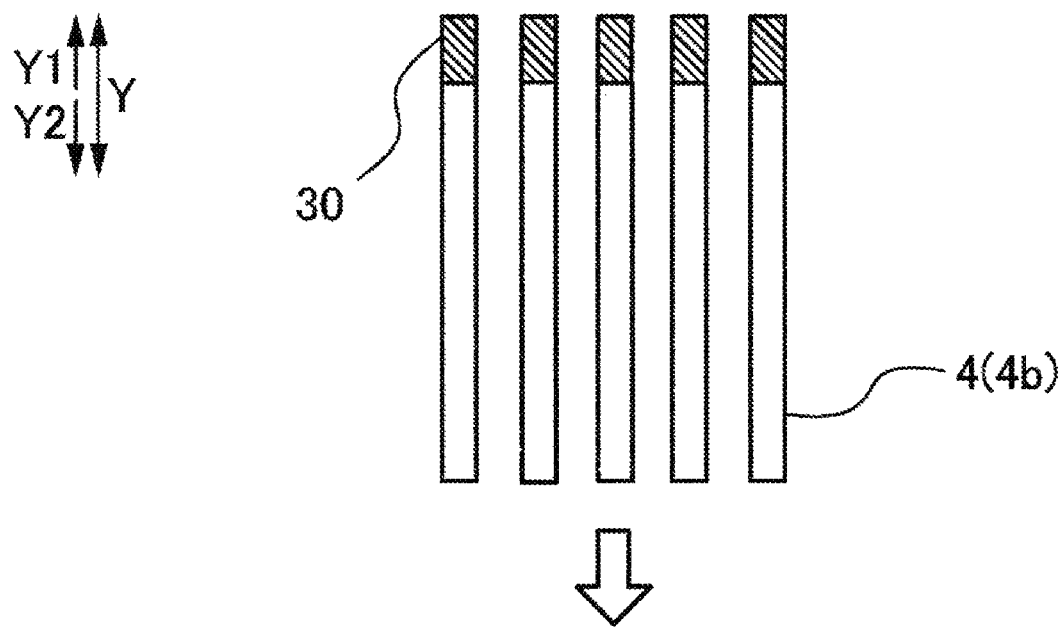
FIG. 10B is a schematic diagram for explaining the positional relationship when the position of the self-image of the first grating is displaced in the Y-direction when the grating components of the first grating and the second grating are arranged so as to extend in the Y-direction.

FIGS. 10A and 10B are diagrams showing an example in which the positional displacement of the grating occurred in a direction orthogonal to the scanning direction of the grating. In the example shown in FIGS. 10A and 10B, the first grating 3 and the second grating 4 are arranged with the grating components of the gratings oriented in the Y-direction. Therefore, in the example shown in FIGS. 10A and 10B, the scanning direction of the grating is the X-direction.

FIG. 10A is a diagram showing the positional relationship between the self-image 30 of the first grating 3 and the second grating 4 when the first grating 3 and the second grating 4 are in an assumed appropriate positional relationship.

As shown in FIG. 10A, when no positioning displacement of the grating occurred, the position of the self-image 30 of the first grating 3 and the position of the X-ray shielding portion 4b of the second grating 4 in the scanning direction (X direction) of the grating coincides. Therefore, the shape of the step curve obtained by imaging while scanning the first grating 3 in the X-direction from this state has a shape reflecting the shape of the object T. FIG. 10B is a diagram showing the positional relationship between the self-image 30 of the first grating 3 and the second grating 4 when the first grating 3 caused a positional displacement in the Y1-direction. As shown in FIG. 10B, even in cases where the positional displacement occurs in a direction orthogonal to the scanning direction of the grating, since the positional displacement does not occur in the X-direction, compared to the case in which the grating is arranged in an appropriate positional relationship, the intensity of the X-ray detected in the area within the grating plane does not change. Therefore, the shape of the step curve does not change.

As a result, by arranging the grating so that the extending direction of the grating component thereof is oriented in a direction along the direction of the positional displacement due to the grating holder 7, even if the grating caused a positional displacement, it is possible to suppress that the positional displacement affects the shape of the step curve to be acquired. Therefore, in the first embodiment, the plurality of gratings is arranged so that the directions in which the grating components of a plurality of gratings extend are oriented in a direction in which the positional displacement due to the grating holder 7 becomes maximum in a plane orthogonal to the optical axis of the X-ray. As a result, the maximum positional displacement direction and the scanning direction become the relationship of FIG. 10B.

Here, positional displacements due to the grating holder 7 will be considered. Various factors can be considered as positional displacement factors during imaging, but the positional displacements include at least a positional displacement due to heat. The grating holder 7 and the grating position adjustment mechanism 9 are composed of metal members, such as aluminum members. Further, since the grating position adjustment mechanism 9 includes a motor and the like for performing the position adjustment of the grating, it is conceivable that heat is generated. When heat is generated, the grating holder 7 and the grating position adjustment mechanism 9, which are made of a metal member, such as, e.g., an aluminum member, may sometimes cause thermal deformation.

For example, in the case of aluminum, since the thermal expansion coefficient per 1 m is $23 \times 10^{-6}$ [/° C.], assuming that the thickness of the grating holder 7 is 10 cm and that the temperature varies uniformly as a whole, thermal deformation of 2.3 μm per 1° C. will occur. Since the period of each grating is several micrometers (μm) to several tens micrometers (μm), when the position of the grating is displaced by several micrometers (μm) to several tens micrometers (μm), the shape of the step curve will be affected. Therefore, even if the temperature of the grating holder 7 and the grating position adjustment mechanism 9 changes only by several degrees centigrade (° C.), the step curve is affected. In order to suppress such thermal deformation of the grating holder 7 and the grating position adjustment mechanism 9, it is necessary to keep the temperature change within a range of zero point several degrees centigrade (° C.) or less. However, in addition to the ambient temperature change, the grating position adjustment mechanism 9 includes a motor, etc., and therefore heat is generated from the inside. For this reason, it is considered to be difficult to suppress the temperature change in a range of zero point several degrees of centigrade (° C.).

Assuming that a positional displacement occurs uniformly by the thermal deformation, in the configuration according to the first embodiment, in the grating position adjustment mechanism 9, the direction in which the total thickness of the grating position adjustment mechanism 9 is maximum in the Y-direction. Therefore, the positional displacement in the Y-direction is considered to be the maximum. In addition, as shown in FIG. 6, when a plurality of positions of the grating are held by the grating position adjustment mechanism 9, it is considered that the positional displacement in a direction in which the thickness of each grating position adjustment mechanism 9 is large becomes maximum. Therefore, in the example shown in FIG. 6A, the positional displacement occurs in the Y-direction. In the example shown in FIG. 6B, since the thickness of the first adjustment mechanism 9a and the thickness of the second adjustment mechanism 9b are the same, a positional displacement due to the grating holder 7 occurs in the direction of the arrow 10 (in the composite direction of the positional displacements).

Therefore, in the first embodiment, even in cases where the positional displacement of the grating due to the grating holder 7 and the grating position adjustment mechanism 9, such as, e.g., the positional displacement due to the thermal deformation, occurred in the X-ray phase-contrast imaging apparatus 100, a plurality of gratings is arranged so that the extending direction of the grating components of a plurality of gratings is along the direction of the positional displacement due to the grating holder 7 so that the shape of the step curve to be acquired does not change. Concretely, the plurality of gratings is arranged such that the extending direction of the grating components of the plurality of gratings is oriented in a direction (Y-direction) in which a total thickness of the grating position adjustment mechanisms 9 becomes maximum.

Also, as shown in FIG. 6B, the positional displacement direction due to the grating holder 7 and the grating position adjustment mechanism 9 may sometimes become oblique in the composite direction of positional displacements. In that case, since the gratings must be translated diagonally, the structure of the grating position adjustment mechanism 9 becomes complicated. It is also conceivable that the grating is diagonally translated by tilting the grating position adjustment mechanism 9. However, in order to accurately tilt the grating position adjustment mechanism 9 at a fine angle, it is required to separately provide a mechanism for tilting the grating position adjustment mechanism 9, so that the apparatus structure becomes more complicated. Here, the positional displacements of the grating holder 7 and the grating position adjustment mechanism 9 are minute. Therefore, when the composite direction of the positional displacement is decomposed in two directions, the direction in which the positional displacement amount in two directions is larger can be regarded as the direction of the positional displacement of the grating holder 7 and the grating position adjustment mechanism 9.

Therefore, in the first embodiment, it is configured such that the composite direction of the positional displacements is decomposed in two directions and one of the two directions is regarded as a positional displacement direction and the grating is arranged. Concretely, the direction of the positional displacement due to the grating holder 7 is a direction in which a positional displacement amount is larger among the positional displacement amounts obtained by decomposing the positional displacement amount of the grating holder in two different directions in a plane orthogonal to the optical axis of the X-ray irradiated from the X-ray source. More specifically, in the first embodiment, the grating position adjustment mechanism 9 is configured to relatively move the plurality of gratings along a direction orthogonal to a direction in which the positional displacement of the grating holder 7 becomes the maximum. Further, in the first embodiment, the plurality of gratings is arranged such that the extending direction of the grating components of the plurality of gratings is oriented in a direction in which the total thickness of the grating position adjustment mechanisms 9 becomes the maximum.

(Effects of First Embodiments)

In the first embodiment, the following effects can be obtained.

In the first embodiment, as described above, the X-ray phase-contrast imaging apparatus 100 is equipped with the X-ray source 1, the detector 5 for detecting the X-ray irradiated from the X-ray source 1, a plurality of gratings arranged between the X-ray source 1 and the detector 5, the control unit 6 for generating an image (including at least one of the absorption image, the phase differential image, and the dark field image) based on the detection signal of the X-ray which has passed through the plurality of gratings and detected by the detector 5, and the grating holders 7 for holding the respective plurality of gratings. The plurality of gratings is arranged so that the extending direction of the grating components of the plurality of gratings is oriented in the direction in which the positional displacement due to the grating holder 7 becomes the maximum in a plane orthogonal to the optical axis of the X-ray.

With this, by arranging the gratings so that the extending direction of the grating components of the first grating 3 and the second grating 4 is oriented in the direction of the positional displacement due to the grating holder 7, even if a positional displacement due to the grating holder 7 occurs in a plane orthogonal to the optical axis direction of the X-ray, it becomes possible to suppress the change of the positional relationship of gratings in a direction orthogonal to the extending directions of the self-image 30 of the first grating 3 and the grating component of the second grating 4. As a result, it is possible to suppress the change of the shape of the step curve to be acquired. Thus, the image quality of the image to be acquired can be suppressed from being deteriorated even if the gratings cause positional displacements due to the grating holders 7 in a plane orthogonal to the optical axis direction of the X-ray.

Further, in the first embodiment, as described above, the grating holder 7 is further equipped with the grating position adjustment mechanism 9 for adjusting the relative position of the plurality of gratings. The control unit 6 is configured to adjust the relative position of the plurality of gratings by the grating position adjustment mechanism 9. The grating position adjustment mechanism 9 is configured to relatively move the plurality of gratings along a direction orthogonal to a direction in which the positional displacement of the grating holder 7 is the maximum at the time of imaging.

With this configuration, the direction for relatively moving a plurality of gratings and the direction of the positional displacement due to the grating holder 7 can be made orthogonal. Therefore, even if a positional displacement occurs due to the grating holder 7, the positional displacement in the direction for relatively moving the plurality of gratings can be suppressed. As a result, it is possible to suppress the change of the shape of the step curve to be acquired, which can suppress deterioration of the image quality of the image to be generated.

Further, in the first embodiment, as described above, the grating position adjustment mechanism is configured by stacking a plurality of positioning mechanisms for moving the plurality of gratings in different directions. The plurality of gratings is arranged such that the extending direction of the grating components of the plurality of gratings is oriented in the direction in which the total thickness of the grating position adjustment mechanisms 9 becomes the maximum.

Here, in cases where the grating position adjustment mechanism 9 is composed of the same member, for example, the positional displacement of the grating when the grating causes a positional displacement due to the thermal deformation of the grating position adjustment mechanism 9 is considered to depend on the thickness of the grating position adjustment mechanism 9. Therefore, by configuring the gratings such that the extending direction of the grating components of the plurality of gratings is oriented in the direction in which the thickness of the grating position adjustment mechanism 9 becomes maximum, it is possible to analytically determine the direction of the positional displacement without measuring the positional displacement due to the grating position adjustment mechanism 9.

Further, in the first embodiment, as described above, the plurality of gratings includes the first grating 3 for generating a Talbot interference by changing the phase of the X-ray irradiated from the X-ray source 1 and the second grating 4 for shielding a part of the X-ray configuring an image (self-image 30) generated by the Talbot interference by the first grating 3. The first grating 3 and the second grating 4 are arranged such that the extending direction of both grating components of the first grating 3 and the second grating 4 is oriented in a direction in which the positional displacement due to the grating holder 7 becomes maximum in a plane orthogonal to an optical axis of the X-ray.

With this configuration, in a Talbot interferometer requiring strict setting of the positional relationship between the first grating 3 and the second grating 4, it is possible to suppress the deterioration of the image quality due to the positional displacement of the first grating 3 due to the grating holder 7. Therefore, in a Talbot interferometer, it is preferable to use the X-ray phase-contrast imaging apparatus 100 to suppress the deterioration of the image quality of the image due to the positional displacement of the first grating 3 due to the grating holder 7.

Further, in the first embodiment, as described above, the positional displacement due to the grating holder 7 includes a positional displacement due to the thermal deformation of at least the grating holder 7. With this configuration, even in cases where the grating holder 7 is thermally deformed due to the thermal fluctuation occurred around the grating holder 7 during the imaging of the X-ray phase-contrast imaging image, it is possible to suppress the deterioration of the image quality of the image to be acquired due to the positional displacement of the grating due to the grating holder 7.

Further, in the first embodiment, as described above, the direction of the positional displacement due to the grating holder 7 is a direction in which a positional displacement amount is larger among the positional displacement amounts obtained by decomposing the positional displacement amount of the grating holder in two different directions in a plane orthogonal to the optical axis of the X-ray irradiated from the X-ray source. With this configuration, it is possible to regard one direction in which the positional displacement amount of the grating holder 7, which most affects positional displacement of the grating, as a direction of the positional displacement of the grating holder 7. As a result, it is possible to easily determine the arrangement direction of the grating.

Further, in the first embodiment, as described above, the X-ray source 1, the plurality of gratings, and the detector 5 are arranged in a horizontal direction. The direction of the positional displacement due to the grating holder 7 is a direction in which the positional displacement amount is larger among two directions including the vertical direction and the lateral direction of the detector 5 in a plane orthogonal to the optical axis of the X-ray irradiated from the X-ray source 1. With this, even in cases where the X-ray phase-contrast imaging apparatus 100 is arranged in the horizontal direction, it is enough to move the grating in either one of the vertical direction and the lateral direction of the detector 5 in a plane orthogonal to the optical axis of the X-ray, it is easy to move the grating by the grating position adjustment mechanism 9.

Second Embodiment

Figure 11:
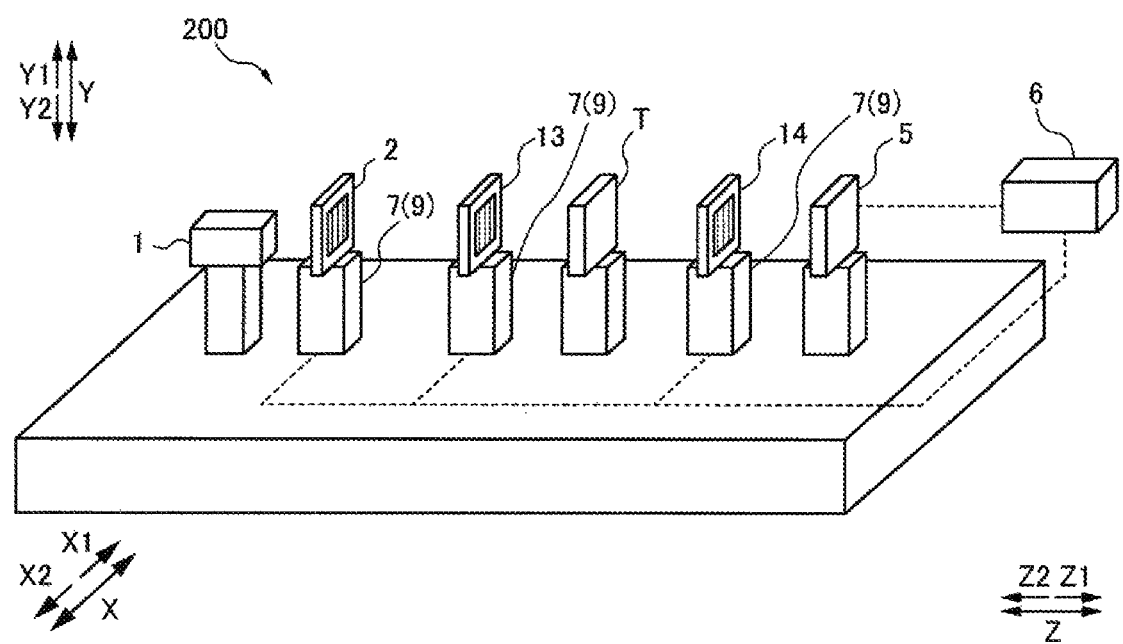
FIG. 11 is a diagram showing an overall structure of an X-ray phase-contrast imaging apparatus according to a second embodiment of the present invention.

With reference to FIG. 11, an X-ray phase-contrast imaging apparatus 200 according to a second embodiment of the present invention will be described. Unlike the first embodiment including the first grating 3 for generating a Talbot interference by changing the phase of the X-ray irradiated from the X-ray source 1 and the second grating 4 for shielding a part of the X-ray configuring the image (self-image 30) generated by the Talbot interference by the first grating 3, in the second embodiment, a third grating 2 for shielding a part of the X-ray irradiated from the X-ray source 1 and a fourth grating 13 for shielding a part of the X-ray forming an image generated by shielding a part of the X-ray by the third grating 2 are included. The same reference numerals are allotted to the same configurations as those of the first embodiment, and the description thereof will be omitted.

As shown in FIG. 11, in the X-ray phase-contrast imaging apparatus 200 according to the second embodiment, the plurality of gratings includes the fourth grating 13 for shielding a part of the X-ray irradiated from the X-ray source 1 and the fifth grating 14 for shielding a part of the X-ray forming an image generated by shielding a part of the X-ray by the fourth grating 13 are included. The fourth grating 13 and the fifth grating 14 are arranged such that the extending direction of both grating components of the fourth grating 13 and the fifth grating 14 is oriented in a direction in which the positional displacement due to the grating holder 7 becomes maximum in a plane orthogonal to an optical axis of the X-ray. The fourth grating 13 and the fifth grating 14 are an example of the "third grating" and an example of the "fourth grating" recited in claims, respectively.

The fourth grating 13 and the fifth grating 14 have the same configuration as the second grating 4 and each are a so-called absorption grating.

In the second embodiment, the control unit 6 is configured to generate an absorption image, a phase differential image, and a dark field image by regarding the transmission image of the X-ray that has transmitted through the fourth grating 13 as a self-image 30.

Other configurations of the second embodiment are the same as those of the first embodiment.
(Effects of Second Embodiments)

In the second embodiment, the following effects can be obtained.

In the second embodiment, as described above, the plurality of gratings includes the fourth grating 13 for shielding a part of the X-ray irradiated from the X-ray source 1 and a fifth grating 14 for shielding a part of the X-ray forming an image generated by shielding a part of the X-ray by the fourth grating 13. The fourth grating 13 and the fifth grating 14 are arranged such that the extending direction of both grating components of the fourth grating 13 and the fifth grating 14 is oriented in a direction in which the positional displacement due to the grating holder 7 becomes maximum in a plane orthogonal to an optical axis of the X-ray.

With this, in a non-interferometer, the deterioration of the image quality due to the positional displacement of the grating holder 7 can be suppressed. Therefore, in a non-interferometer, the deterioration of the image quality of the image due to the positional displacement of the fourth grating 13 and/or the fifth grating 14 due to the grating holder 7 can be suppressed. Therefore, in a non-interferometer, it is preferable to use the present invention to suppress the deterioration of the image quality of the image due to the positional displacement of the fourth grating 13 and/or the fifth grating 14 due to the grating holder 7.

Other effects of the second embodiment are the same as those of the first embodiment.

Third Embodiment

Figure 12:
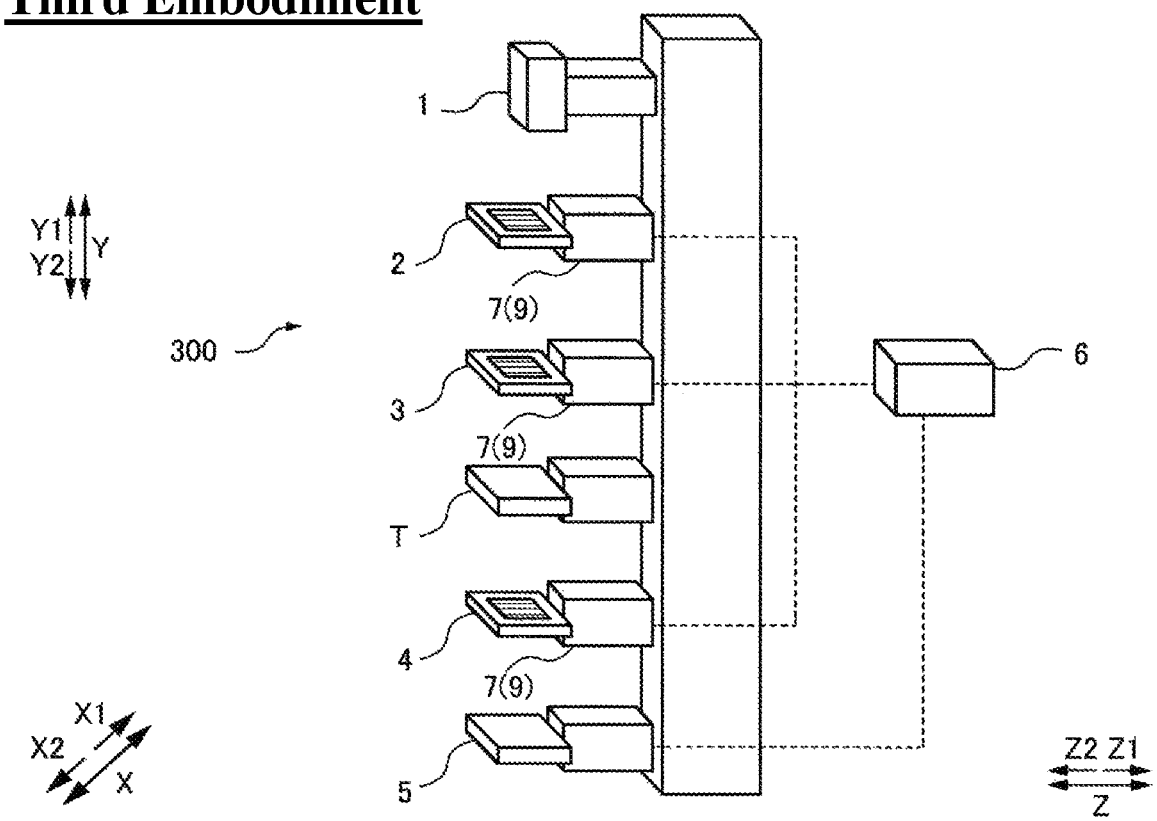
FIG. 12 is a diagram showing an overall structure of an X-ray phase-contrast imaging apparatus according to a third embodiment of the present invention.

With reference to FIG. 12, an X-ray phase-contrast imaging apparatus 300 according to a third embodiment of the present invention will be described. Unlike the first embodiment in which the X-ray source 1, the plurality of gratings, and the detector 5 are arranged in a horizontal direction (Z-direction), the X-ray source 1, the plurality of gratings, and the detector 5 are arranged in a vertical direction (Y-direction). The same reference numerals are allotted to the same configurations as those of the first embodiment, and the description thereof will be omitted.

As shown in FIG. 11, in the X-ray phase-contrast imaging apparatus 300 according to the third embodiment, the X-ray source 1, the plurality of gratings, and the detector 5 are arranged in a vertical direction (Y-direction). The direction of the positional displacement due to the grating holder 7 is a direction in which the positional displacement amount is larger among two directions including the vertical direction and the lateral direction of the detector 5 in a plane (horizontal plane) orthogonal to the optical axis of the X-ray irradiated from the X-ray source 1.

Other configurations of the third embodiment are the same as those of the first embodiment.
(Effects of Third Embodiment)

In the third embodiment, the following effects can be obtained.

In the third embodiment, as described above, the X-ray source 1, the plurality of gratings, and the detector 5 are arranged in the vertical direction (Y-direction). The direction of the positional displacement due to the grating holder 7 is a direction in which the positional displacement amount is larger among two directions including the vertical direction and the lateral direction of the detector 5 in a plane (horizontal plane) orthogonal to the optical axis of the X-ray irradiated from the X-ray source 1. With this, even in cases where the X-ray phase-contrast imaging apparatus 300 is arranged in the vertical direction (Y-direction), it is enough to move the grating to either one of the vertical direction and the lateral direction of the detector 5 in a plane orthogonal to the optical axis of the X-ray, and therefore it is easy to move the grating by the grating position adjustment mechanism 9.

Other configurations of the third embodiment are the same as those of the first embodiment.

(Modifications)

It should be understood that the embodiments disclosed here are examples in all respects and are not restrictive. The scope of the present invention is shown by the scope of the claims rather than the descriptions of the embodiments described above, and include all changes (modifications) within the meaning of equivalent and the scope of claims.

For example, in the first and second embodiments, the example in which the extending direction of the grating components of the plurality of gratings is oriented in the Y-direction is shown, but the present invention is not limited thereto. For example, as long as the positional displacement direction due to the grating holder 7 is the X-direction, it may be configured so that the extending direction of the grating component of the plurality of gratings is oriented in the X-direction.

Figure 13:
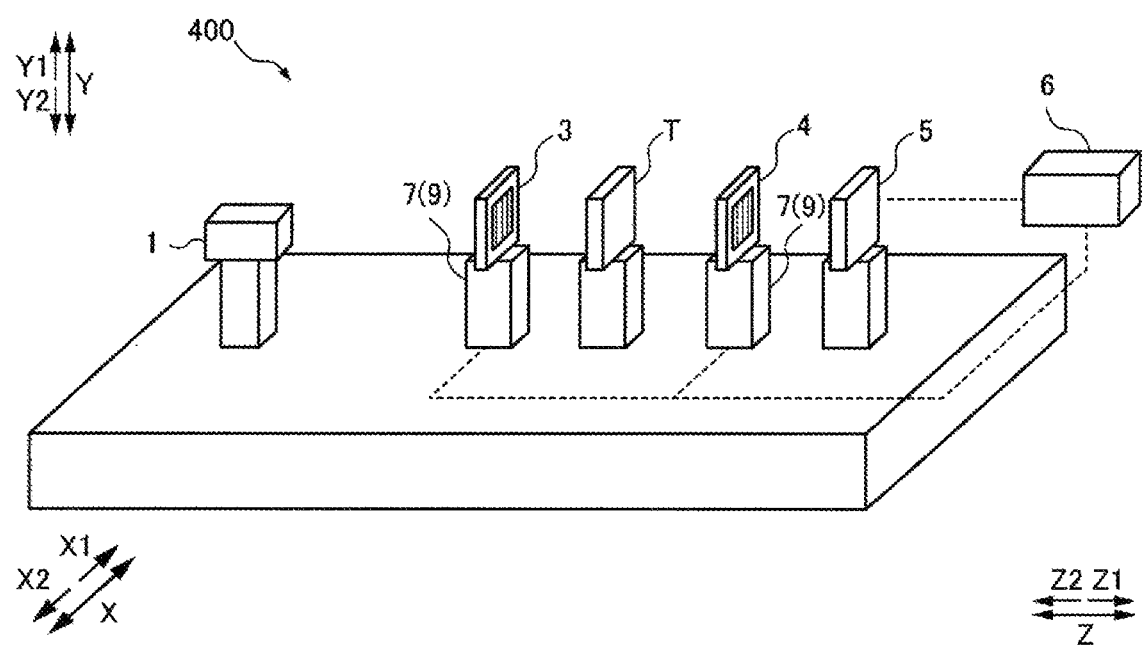
FIG. 13 is a diagram showing an overall structure of an X-ray phase-contrast imaging apparatus according to a first modification of the first embodiment of the present invention.

Further, in the aforementioned embodiment, the example in which the third grating 2 is provided is shown, but the present invention is not limited thereto. For example, when the coherence of the X-ray irradiated from the X-ray source 1 is high, as shown in FIG. 13, the third grating 2 may not be provided.

In the aforementioned embodiment, the example in which the positional displacement of the grating holder 7 and the grating position adjustment mechanism 9 is caused by the thermal deformation, but the present invention is not limited thereto. Even if the grating holder 7 and the grating position adjustment mechanism 9 cause positional displacements due to factors other than the thermal deformation, it is enough to arrange the gratings so that the direction of the positional displacement and the extending direction of the grating components of the plurality of gratings match.

Further, in the first and second embodiments, the example in which the grating holder 7 holds each grating from the lower side (Y1-direction), but the present invention is not limited thereto. For example, it may be configured to suspend the grating holder 7 and hold each grating from above (Y2-direction).

Further, in the aforementioned embodiments, the example in which the gratings are arranged such that the grating components are oriented in a direction along the direction in which the thickness of the grating position adjustment mechanism 9 becomes the maximum, but the present invention is not limited thereto. For example, it may be configured such that the positional displacement of the grating is measured by changing the installation environment temperature of the X-ray phase-contrast imaging apparatus, the direction in which the positional displacement of the grating is the maximum is determined, and the gratings are arranged so that the grating components of the gratings move along a determined direction.

Figure 14:
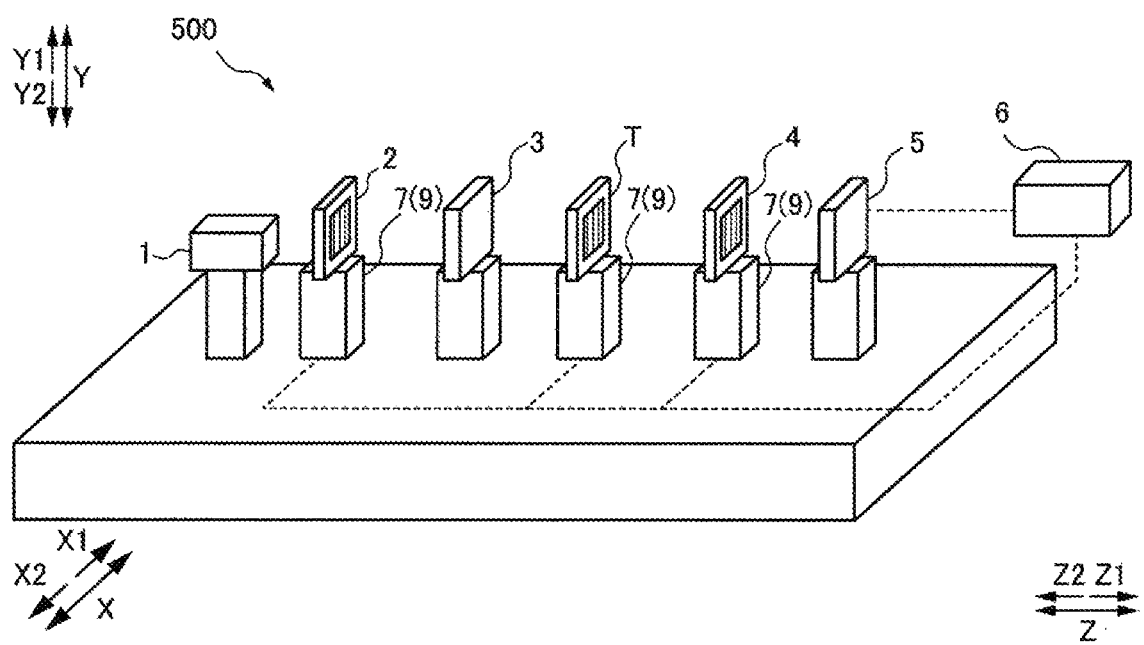
FIG. 14 is a diagram showing an overall structure of an X-ray phase-contrast imaging apparatus according to a second modification of the first embodiment of the present invention.

Further, in the aforementioned embodiment, the example in which the object T is arranged between the first grating 3 (fourth grating 13) and the second grating 4 (the fifth grating 14) are shown, but the present invention is not limited thereto. For example, as shown in FIG. 14, the object T may be arranged between the third grating 2 and the first grating 3 (fourth grating 13). However, since an image with high image quality can be generated when the object T is arranged between the first grating 3 (fourth grating 13) and the second grating 4 (fifth grating 14). Therefore, it is preferable to arrange the object T between the first grating 3 (fourth grating 13) and the second grating 4 (fifth grating 14).

Further, in the aforementioned embodiment, the example in which the second grating 4 (fifth grating 14) provided is shown, but the present invention is not limited thereto. For example, when the pixel size of the detector 5 is fine, it is possible to directly detect the self-image 30 of the first grating 3, so it may be configured to not include the second grating 4 (fifth grating 14).

The invention claimed is:

1. An X-ray phase-contrast imaging apparatus comprising:
   an X-ray source;
   a detector configured to detect an X-ray irradiated from the X-ray source;
   a plurality of gratings arranged between the X-ray source and the detector;
   a control unit configured to generate an image based a detection signal of the X-ray that has passed through the plurality of gratings and detected by the detector; and
   grating holders each configured to hold a corresponding one of the plurality of gratings,
   wherein the plurality of gratings are arranged such that an extending direction of grating components of the plurality of gratings is oriented in a direction in which a total thickness of the grating holder becomes maximum.

2. The X-ray phase-contrast imaging apparatus as recited in claim 1, wherein
   a first grating holder of the plurality of grating holders is further equipped with a grating position adjustment mechanism for adjusting a relative position of the plurality of gratings,
   the control unit is configured to adjust the relative position of the plurality of gratings by the grating position adjustment mechanism, and
   the grating position adjustment mechanism is configured to relatively move the plurality of gratings along a direction orthogonal to a direction in which a total thickness of the grating holder becomes maximum at the time of imaging.

3. The X-ray phase-contrast imaging apparatus as recited in claim 2, wherein
   the grating position adjustment mechanism is configured by stacking a plurality of positioning mechanisms for relatively moving the plurality of gratings in different directions, and
   the plurality of gratings are arranged such that the extending direction of the grating components of the plurality of gratings is oriented in a direction in which a total thickness of the grating position adjustment mechanisms becomes maximum.

4. The X-ray phase-contrast imaging apparatus as recited in claim 2, wherein
the plurality of gratings includes a first grating for generating a Talbot interference by changing a phase of the X-ray irradiated from the X-ray source and a second grating for shielding a part of the X-ray forming an image generated by the Talbot interference by the first grating, and
the first grating and the second grating are arranged such that the extending direction of both grating components of the first grating and the second grating is oriented in a direction in which a total thickness of the grating holder becomes maximum.

5. The X-ray phase-contrast imaging apparatus as recited in claim 2, wherein
the plurality of gratings includes a third grating for shielding a part of the X-ray irradiated from the X-ray source and a fourth grating for shielding a part of the X-ray forming an image generated by shielding a part of the X-ray by the third grating, and
the third grating and the fourth grating are arranged such that the extending direction of both grating components of the third grating and the fourth grating is oriented in a direction in which a total thickness of the grating holder becomes maximum.

6. The X-ray phase-contrast imaging apparatus as recited in claim 1, wherein
the plurality of gratings are arranged such that an extending direction of the grating components of the plurality of gratings is oriented in a direction in which the positional displacement due to the grating holder becomes maximum in a plane orthogonal to an optical axis of the X-ray, and
the positional displacement due to the grating holder includes a positional displacement due to at least thermal deformation of the grating holder.

7. The X-ray phase-contrast imaging apparatus as recited in claim 1, wherein
the plurality of gratings further include a fifth grating for enhancing spatial coherence of the X-ray by shielding a part of the X-ray irradiated from the X-ray source.

8. An X-ray phase-contrast imaging apparatus comprising:
an X-ray source;
a detector configured to detect an X-ray irradiated from the X-ray source;
a plurality of gratings arranged between the X-ray source and the detector;
a control unit configured to generate an image based a detection signal of the X-ray that has passed through the plurality of gratings and detected by the detector; and
grating holders each configured to hold a corresponding one of the plurality of gratings,
wherein the plurality of gratings are arranged such that an extending direction of the grating components of the plurality of gratings is oriented in a direction in which a positional displacement due to the grating holder becomes maximum in a plane orthogonal to an optical axis of the X-ray, and
wherein the direction of the positional displacement due to a first grating holder of the plurality of grating holders is a direction in which a positional displacement amount is larger among the positional displacement amounts obtained by decomposing the positional displacement amount of the first grating holder in two different directions in a plane orthogonal to the optical axis of the X-ray irradiated from the X-ray source.

9. The X-ray phase-contrast imaging apparatus as recited in claim 8, wherein
the X-ray source, the plurality of gratings, and the detector are arranged in a horizontal direction or a vertical direction, and
the direction of the positional displacement due to the grating holder is a direction in which the positional displacement amount is larger among two directions including the vertical direction and the lateral direction of the detector in the plane orthogonal to the optical axis of the X-ray irradiated from the X-ray source.

* * * * *